(12) United States Patent
Naito et al.

(10) Patent No.: US 11,170,985 B2
(45) Date of Patent: *Nov. 9, 2021

(54) SURFACE-ASSISTED LASER DESORPTION/IONIZATION METHOD, MASS SPECTROMETRY METHOD AND MASS SPECTROMETRY DEVICE

(71) Applicant: HAMAMATSU PHOTONICS K.K., Hamamatsu (JP)

(72) Inventors: Yasuhide Naito, Hamamatsu (JP); Masahiro Kotani, Hamamatsu (JP); Takayuki Ohmura, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/864,919

(22) Filed: May 1, 2020

(65) Prior Publication Data

US 2020/0258730 A1    Aug. 13, 2020

Related U.S. Application Data

(63) Continuation of application No. 16/238,250, filed on Jan. 2, 2019, now Pat. No. 10,679,835, which is a (Continued)

(30) Foreign Application Priority Data

Sep. 3, 2015   (JP) ................... 2015-173590

(51) Int. Cl.
*H01J 49/04*   (2006.01)
*G01N 27/62*   (2021.01)
(Continued)

(52) U.S. Cl.
CPC ........ *H01J 49/0418* (2013.01); *G01N 1/2806* (2013.01); *G01N 1/2813* (2013.01);
(Continued)

(58) Field of Classification Search
CPC ...... H01J 49/0418; H01J 49/164; H01J 49/26; G01N 1/2806; G01N 1/2813; G01N 27/62; G01N 33/6851
See application file for complete search history.

(56) References Cited

U.S. PATENT DOCUMENTS 5,828,063 A    10/1998    Köster et al.
6,071,610 A     6/2000    Jarrell et al.
(Continued)

FOREIGN PATENT DOCUMENTS

CN    101105473        1/2008
CN    101228445 A      7/2008
(Continued)

OTHER PUBLICATIONS

English-language translalon of International Preliminary Report on Patentability (IPRP) dated Mar. 15, 2018 that issued in WO Patent Application No. PCT/JP2016/075049.
(Continued)

*Primary Examiner* — Nicole M Ippolito
*Assistant Examiner* — Hanway Chang
(74) *Attorney, Agent, or Firm* — Faegre Drinker Biddle & Reath LLP

(57) ABSTRACT

A surface-assisted laser desorption/ionization method according to an aspect includes: a first process of preparing a sample support (2) having a substrate (21) in which a plurality of through-holes (S) passing from one surface (21a) thereof to the other surface (21b) thereof are provided and a conductive layer (23) that covers at least the one surface (21a); a second process of placing a sample (10) on
(Continued)

a sample stage (1) and arranging the sample support (2) on the sample (10) such that the other surface (21*b*) faces the sample (10); and a third process of applying a laser beam (L) to the one surface (21*a*) and ionizing the sample (10) moved from the other surface (21*b*) side to the one surface (21*a*) side via the through-holes (S) due to a capillary phenomenon.

10 Claims, 18 Drawing Sheets

Related U.S. Application Data continuation of application No. 15/571,568, filed as application No. PCT/JP2016/075049 on Aug. 26, 2016, now Pat. No. 10,224,195.

(51) Int. Cl.
  *G01N 1/28*       (2006.01)
  *G01N 33/68*      (2006.01)
  *H01J 49/16*      (2006.01)
  *H01J 49/26*      (2006.01)

(52) U.S. Cl.
  CPC ......... *G01N 27/62* (2013.01); *G01N 33/6851* (2013.01); *H01J 49/164* (2013.01); *H01J 49/26* (2013.01)

(56) References Cited

U.S. PATENT DOCUMENTS

| | | | |
|---|---|---|---|
| 6,139,713 A | 10/2000 | Masuda et al. | |
| 6,288,390 B1 | 9/2001 | Siuzdak et al. | |
| 6,399,177 B1 | 6/2002 | Fonash et al. | |
| 7,030,373 B2 | 4/2006 | Vestal et al. | |
| 7,232,688 B2 | 6/2007 | Little et al. | |
| 7,332,271 B2 | 2/2008 | O'Keefe et al. | |
| 7,695,978 B2 | 4/2010 | Laprade et al. | |
| 7,759,139 B2 | 7/2010 | Chu et al. | |
| 8,237,114 B2 | 8/2012 | Okuno et al. | |
| 8,558,169 B2 | 10/2013 | Hori et al. | |
| 9,460,921 B2 | 10/2016 | Bertness et al. | |
| 9,490,113 B2 | 11/2016 | Vertes et al. | |
| 9,624,101 B2 | 4/2017 | Mardilovich et al. | |
| 10,224,195 B2 * | 3/2019 | Naito | G01N 1/2806 |
| 10,244,195 B2 * | 3/2019 | Hyun | G08C 23/04 |
| 2002/0011562 A1 | 1/2002 | Park | |
| 2002/0151040 A1 | 10/2002 | O'Keefe et al. | |
| 2004/0096914 A1 | 5/2004 | Fang et al. | |
| 2004/0228772 A1 | 11/2004 | Chen et al. | |
| 2004/0248318 A1 | 12/2004 | Weinberger et al. | |
| 2005/0116161 A1 | 6/2005 | Hafeman et al. | |
| 2005/0133714 A1 | 6/2005 | Vestal et al. | |
| 2006/0176481 A1 | 8/2006 | Forest et al. | |
| 2007/0075241 A1 | 4/2007 | Kim | |
| 2008/0054176 A1 | 3/2008 | Hiraoka | |
| 2008/0090267 A1 | 4/2008 | Komatsu et al. | |
| 2009/0071834 A1 | 3/2009 | Hafeman et al. | |
| 2009/0197295 A1 | 8/2009 | Fournier et al. | |
| 2009/0314936 A1 | 12/2009 | Okuno | |
| 2010/0016171 A1 | 1/2010 | Wong et al. | |
| 2010/0065735 A1 | 3/2010 | Murakami et al. | |
| 2010/0261159 A1 | 10/2010 | Hess et al. | |
| 2013/0034690 A1 | 2/2013 | Law et al. | |
| 2013/0146758 A1 | 6/2013 | Urban et al. | |
| 2017/0358436 A1 | 12/2017 | Naito et al. | |

FOREIGN PATENT DOCUMENTS

| | | |
|---|---|---|
| CN | 102194642 A | 9/2011 |
| CN | 102445489 A | 5/2012 |
| CN | 202443016 U | 9/2012 |
| CN | 102884427 | 1/2013 |
| JP | H10-513546 A | 12/1998 |
| JP | 2004-184137 A | 7/2004 |
| JP | 2007-192673 A | 8/2007 |
| JP | 2008-41648 A | 2/2008 |
| JP | 2008-61648 A | 3/2008 |
| JP | 2008-96245 A | 4/2008 |
| JP | 2009-504161 A | 2/2009 |
| JP | 2009-080106 A | 4/2009 |
| JP | 2009-236489 | 10/2009 |
| JP | 2009-535631 A | 10/2009 |
| JP | 2010-71727 A | 4/2010 |
| JP | 2010-175338 A | 8/2010 |
| JP | 5129628 B2 | 1/2013 |
| JP | 2013-526700 A | 6/2013 |
| JP | 2014-21048 A | 2/2014 |
| JP | 2014-153183 A | 8/2014 |
| WO | WO 96/03768 A1 | 2/1996 |
| WO | WO 00/74932 A1 | 12/2000 |
| WO | WO 01/46695 A1 | 6/2001 |
| WO | 2004-500481 A | 1/2004 |
| WO | WO 2007/022026 A2 | 2/2007 |
| WO | WO 2009/069816 A1 | 6/2009 |
| WO | WO 2011/140492 A2 | 11/2011 |

OTHER PUBLICATIONS

English-language translation of International Preliminary Report on Patentability (IPRP) dated Mar. 15, 2018 that issued in WO Patent Application No. PCT/JP2016/075050.

Wang Fangli et al., "Nanomaterial-Based Surface-Assisted Laser Desorption Ionization Mass Spectroscopy", Progress in Chemistry, vol. 27, No. 5, May 6, 2015, p. 571-p. 584.

Jing Wei et al., "Desorption-ionization mass spectrometry on porous silicon", Nature, vol. 399, No. 6733, May 20, 1999, p. 243-p. 246.

\* cited by examiner

Fig.8
(c) 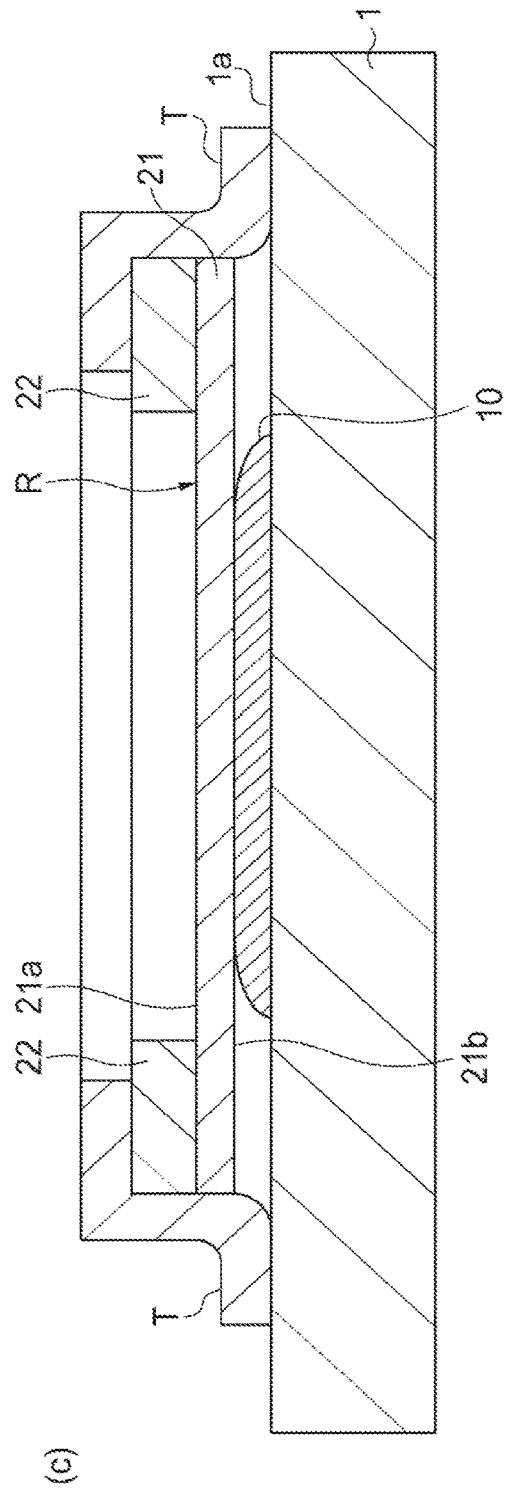
(d) 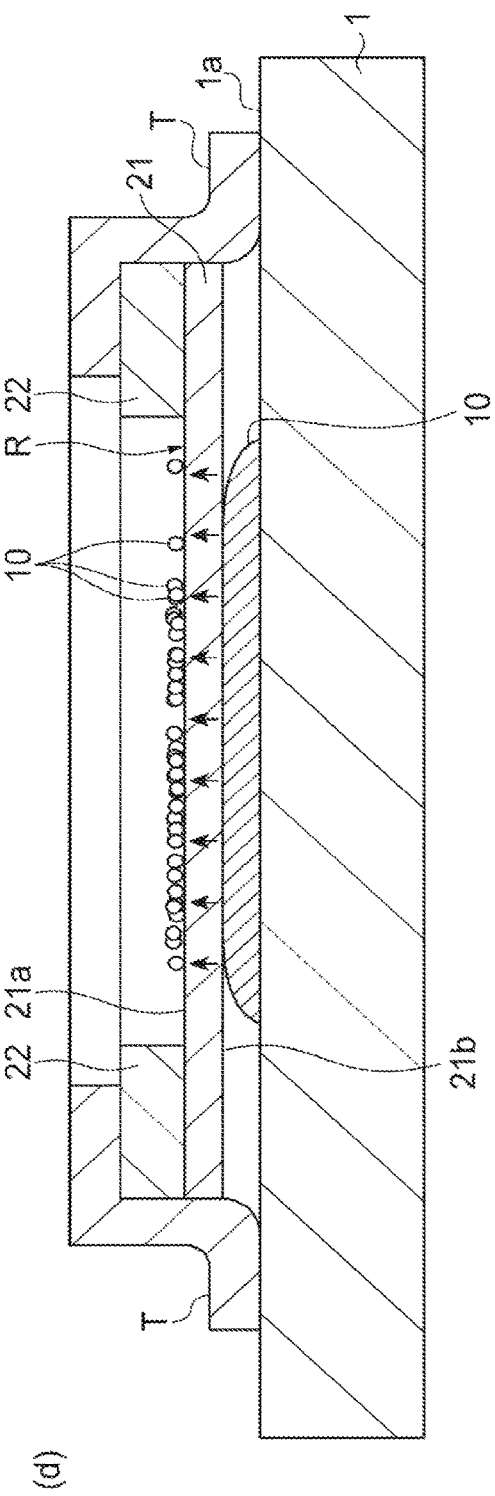

*Fig.13*
(g)
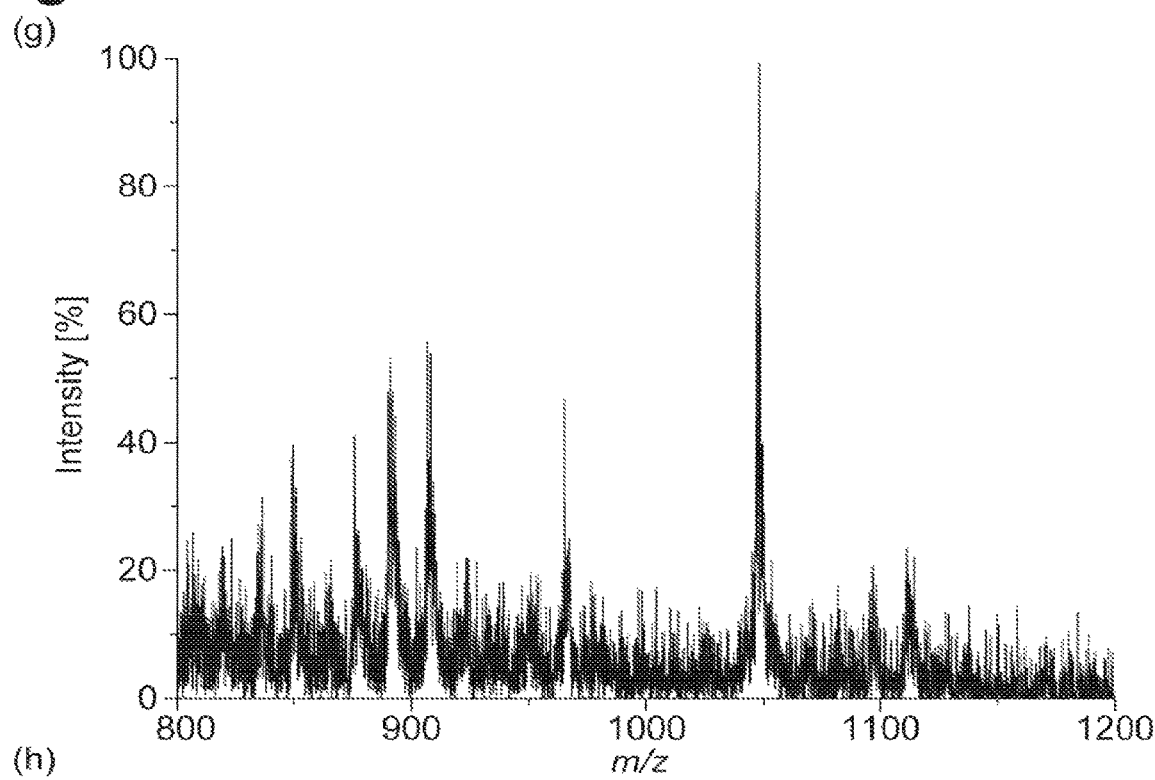
(h)
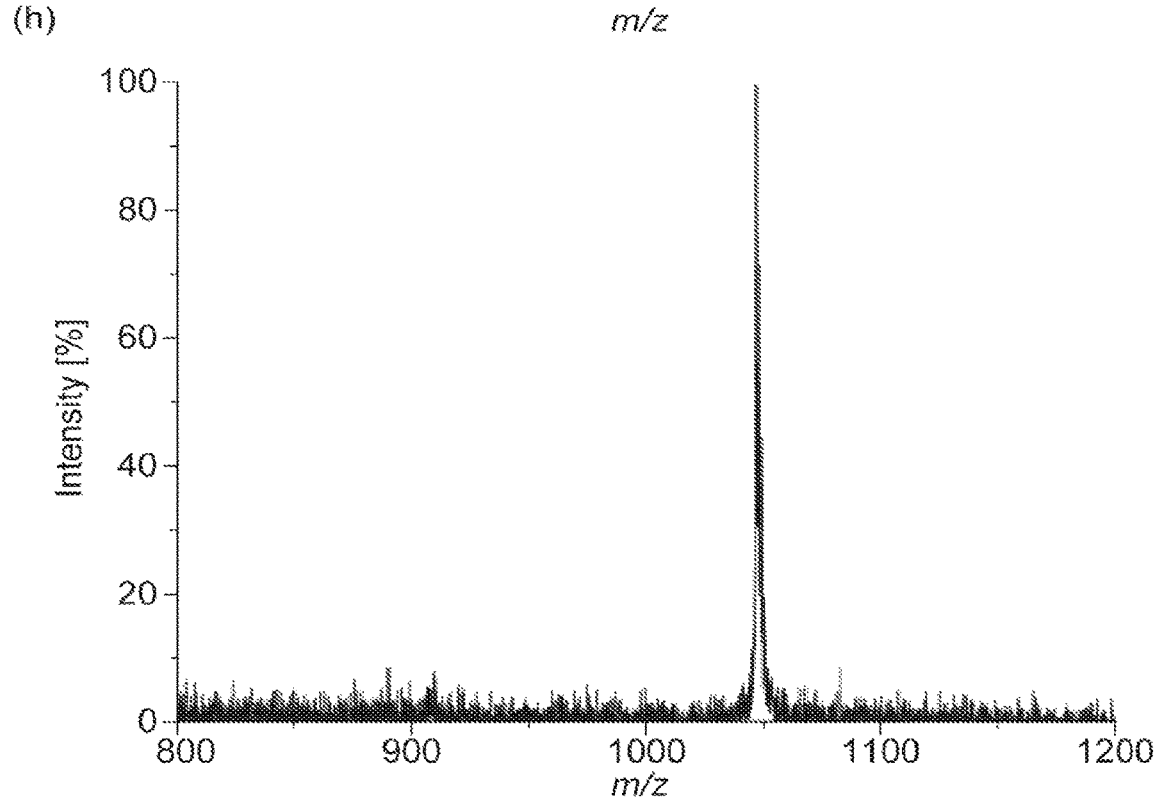

SURFACE-ASSISTED LASER DESORPTION/IONIZATION METHOD, MASS SPECTROMETRY METHOD AND MASS SPECTROMETRY DEVICE

TECHNICAL FIELD

The present invention relates to a surface-assisted laser desorption/ionization method, a mass spectrometry method and a mass spectrometry device.

BACKGROUND ART

As a technique for ionizing a sample such as a biological sample in order to perform mass spectrometry or the like, matrix-assisted laser desorption/ionization (MALDI) has been known thus far. MALDI is a technique for ionizing a sample by mixing the sample with a low-molecular weight organic compound, called a matrix, absorbing an ultraviolet laser beam, and applying the laser beam to the mixture. According to this technique, a heat-labile substance or a high-molecular weight substance can be subjected to non-destructive ionization (so-called soft ionization). However, MALDI generates background noise derived from the matrix.

As a technique for performing ionization without using such a matrix, surface-assisted laser desorption/ionization (SALDI) for ionizing a sample by using a substrate whose surface has an uneven microstructure is known. For example, as an ionization method of a sample according to SALDI, there is a method of using a surface having anodized porous alumina, anodized porous silicon, or the like having fine concavities as a sample holding surface (see Patent Literatures 1 and 2 below). In this ionization method, a sample to be analyzed is dropped onto the sample holding surface having the fine concavities, and a laser beam is applied after drying the sample to ionize the sample.

CITATION LIST

Patent Literature

[Patent Literature 1] Japanese Patent No. 5129628
[Patent Literature 2] U.S. Pat. No. 6,288,390

SUMMARY OF INVENTION

Technical Problem

However, in the above ionization method, since a positional deviation of the sample with respect to the substrate occurs when dropping the sample, it is difficult to ionize the sample while maintaining original position information of the sample (a two-dimensional distribution of molecules composing the sample). For this reason, it is difficult to measure what kind of and how many molecules are present at each position of a sample region and use the ionization method in imaging mass spectrometry or the like imaging a two-dimensional distribution map of the sample molecules. Even when a method of transferring the sample to the substrate instead of dropping the sample onto the substrate is adopted, there is a problem in that a positional deviation of the sample with respect to the substrate occurs when transferring the sample or an uneven transfer of the sample occurs.

Therefore, an aspect of the present invention is directed to providing a surface-assisted laser desorption/ionization method capable of ionizing a sample while maintaining positional information of the sample, a mass spectrometry method, and a mass spectrometry device.

Solution to Problem

A surface-assisted laser desorption/ionization method according to an aspect of the present invention includes: a first process of preparing a sample support having a substrate in which a plurality of through-holes passing from one surface thereof to the other surface thereof are provided and a conductive layer that is formed of a conductive material and covers at least the one surface; a second process of placing a sample on a sample stage and arranging the sample support on the sample such that the other surface faces the sample; and a third process of applying a laser beam to the one surface and ionizing a sample moved from the other surface side to the one surface side via the through-holes due to a capillary phenomenon.

According to the surface-assisted laser desorption/ionization method, the substrate in which the plurality of through-holes are provided is arranged on the sample, and thereby the sample can be raised from the other surface side toward the one surface side of the substrate via the through-holes due to the capillary phenomenon. Thereby, the sample can be moved from the other surface side to the one surface side of the substrate while positional information of the sample (two-dimensional distribution of molecules composing the sample) is maintained. The laser beam is applied to the one surface of the substrate, and energy thereof is transmitted to a sample moved to the one surface side via the conductive layer. Thereby, the sample is ionized. As a result, the sample can be ionized while the positional information of the sample is maintained. Therefore, according to the aforementioned method, the sample can be ionized by a simple operation in which the substrate in which the plurality of through-holes are provided is placed on the sample while the positional information of the sample is maintained.

The substrate may be formed by anodizing a valve metal or silicon. The valve metal or silicon is anodized, and thereby the sample support having the substrate in which the plurality of through-holes are provided is used. Thereby, the movement of the sample caused by the aforementioned capillary phenomenon can be properly realized.

Each of the through-holes may have a width of 1 to 700 nm. The substrate having the through-holes each having the hole width of 1 to 700 nm is used, and thereby the movement of the sample caused by the aforementioned capillary phenomenon can be more smoothly performed. Sufficient signal intensity can be obtained in mass spectrometry using the surface-assisted laser desorption/ionization method.

The substrate may have a thickness of 5 to 10 μm. Thereby, strength of the substrate can be ensured, and sufficient signal intensity can be obtained in mass spectrometry using the surface-assisted laser desorption/ionization method.

The sample support may further include a frame mounted on an outer edge of the one surface of the substrate. Bending of the substrate is suppressed by the frame, and the sample support is easily handled when supported or moved. As a result, an arrangement of the sample support on the sample in the second process can be easily performed.

In the second process, the sample support may be fixed to the sample stage. As the sample support is fixed to the sample stage, the sample and the sample support are brought into close contact with each other, and movement of the sample caused by the capillary phenomenon can be smoothly performed. Sideslippage of the sample support arranged on the sample can be prevented, and a positional deviation of the sample caused by the sideslippage of the sample support can be suppressed.

A surface-assisted laser desorption/ionization method according to another aspect of the present invention includes: a first process of preparing a sample support having a substrate which is formed of a conductive material and in which a plurality of through-holes passing from one surface thereof to the other surface thereof are provided; a second process of placing a sample on a sample stage and arranging the sample support on the sample such that the other surface is in contact with the sample; and a third process of applying a laser beam to the one surface and ionizing a sample moved from the other surface side to the one surface side via the through-holes due to a capillary phenomenon.

In the surface-assisted laser desorption/ionization method, the substrate formed of a conductive material is used. Thereby, the conductive layer can be omitted, and the same effects as when the sample support having the aforementioned conductive layer is used can be obtained.

A mass spectrometry method according to an aspect of the present invention includes: each of the processes of the surface-assisted laser desorption/ionization method; and a fourth process of detecting the sample ionized in the third process, wherein the application of the laser beam in the third process and the detection of the ionized sample in the fourth process are performed at each application position while changing application positions of the laser beam.

According to the mass spectrometry method, the sample can be ionized by a simple operation in which the sample support is arranged on the sample while positional information of the sample is maintained. While changing the application positions of the laser beam, the ionized sample is detected at each application position, and thereby two-dimensional distribution of sample molecules can be perceived. Therefore, according to the mass spectrometry method, imaging mass spectrometry for imaging a two-dimensional distribution map of the sample molecules can be performed by a simple operation.

A mass spectrometry device according to an aspect of the present invention includes: a sample stage on which a sample is placed; a laser beam application unit configured to, in a state in which a sample support, which has a substrate in which a plurality of through-holes passing from one surface thereof to the other surface thereof are provided and a conductive layer that is formed of a conductive material and covers at least the one surface, is arranged on the sample placed on the sample stage such that the other surface faces the sample, apply a laser beam to the one surface while changing application positions thereof; and a detection unit configured to detect a sample ionized by the application of the laser beam at each of the application positions.

According to the mass spectrometry device, the sample can be ionized by a simple operation in which the sample support is arranged on the sample while positional information of the sample is maintained. The laser beam application unit applies the laser beam while changing the application positions of the laser beam, and the detection unit detects the ionized sample at each application position. Thereby, two-dimensional distribution of sample molecules can be perceived. Therefore, according to the mass spectrometry device, imaging mass spectrometry for imaging a two-dimensional distribution map of the sample molecules can be performed by a simple operation.

A mass spectrometry device according to another aspect of the present invention includes: a sample stage on which a sample is placed; a laser beam application unit configured to, in a state in which a sample support, which has a substrate which is formed of a conductive material and in which a plurality of through-holes passing from one surface thereof to the other surface thereof are provided, is arranged on the sample stage placed on the sample stage such that the other surface is in contact with the sample, apply a laser beam to the one surface while changing application positions thereof; and a detection unit configured to detect a sample ionized by the application of the laser beam at each of the application positions.

According to the mass spectrometry device, the substrate formed of a conductive material is used. Thereby, the conductive layer can be omitted, and the same effects as when the sample support having the aforementioned conductive layer is used can be obtained.

Advantageous Effects of Invention

According to the present invention, a surface-assisted laser desorption/ionization method capable of ionizing a sample while maintaining positional information of the sample, a mass spectrometry method, and a mass spectrometry device can be provided.

BRIEF DESCRIPTION OF DRAWINGS

FIG. 8 is a view illustrating a procedure of the mass spectrometry method according to the present embodiment.

FIG. 13 is a view illustrating a relation between the hole width of the through-hole and the mass spectrum.

DESCRIPTION OF EMBODIMENTS

Figure 1:
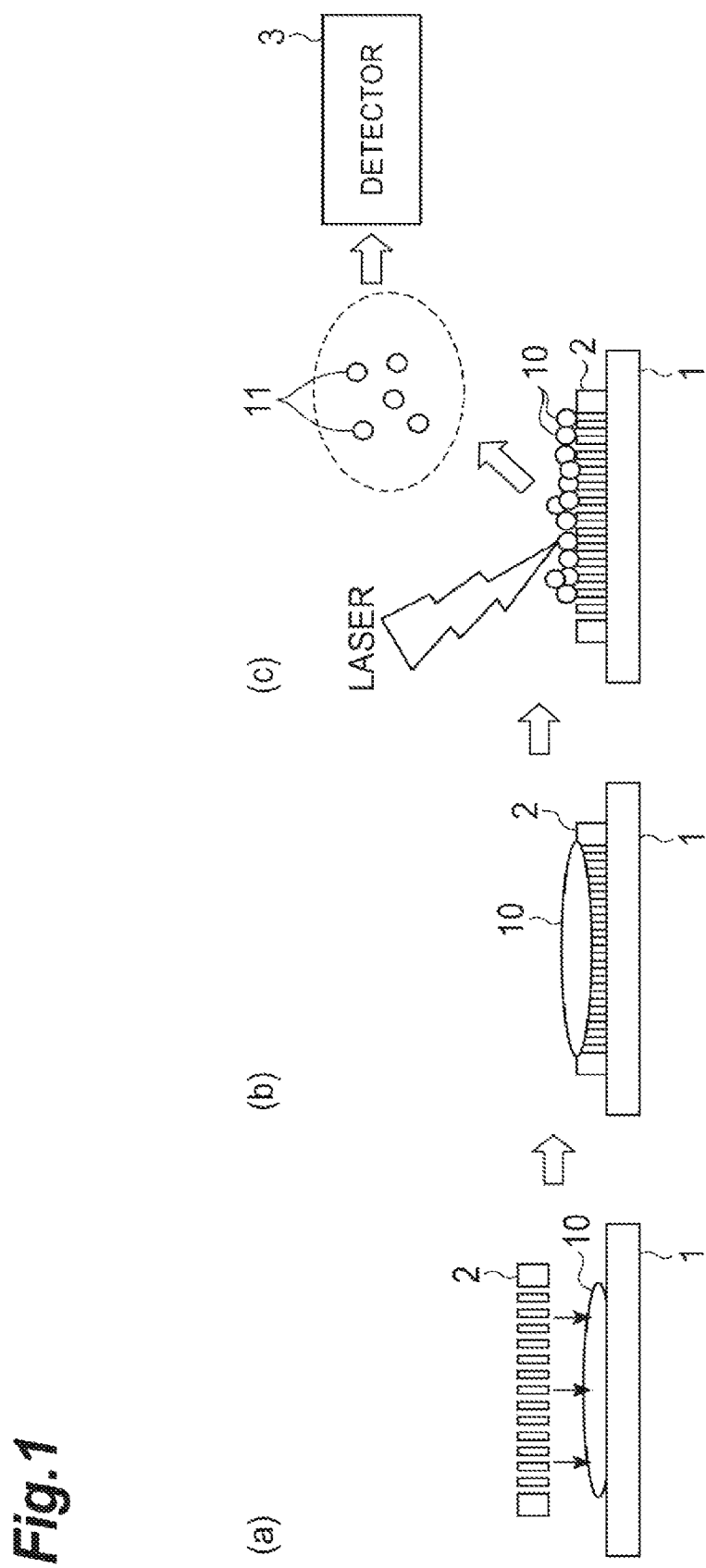
FIG. 1 is a diagram illustrating an outline of a mass spectrometry method according to an embodiment of the present invention.

Hereinafter, preferred embodiments of the present invention will be described in detail with reference to the drawings. Note that the same or equivalent portions are denoted by the same reference signs in each of the drawings, and duplicate descriptions thereof will be omitted. Dimensions of each member (or region) illustrated in the drawings or a ratio of the dimensions may be different from actual dimensions or a ratio of the actual dimensions in order to facilitate an understanding of the description.

An outline of a mass spectrometry method (including a surface-assisted laser desorption/ionization (SALDI) method) according to the present embodiment will be described using FIG. 1. As illustrated in (a) of FIG. 1, in the mass spectrometry method, first, one sample 10 to be subjected to mass spectrometry is placed on a sample stage 1. Further, a sample support 2 having a substrate in which a plurality of through-holes are provided is arranged on the sample 10. Here, the sample 10 to be subjected to spectrometry is a thin film-like biological sample (a hydrous sample) such as a tissue section.

Subsequently, as illustrated in (b) of FIG. 1, the sample 10 is moved from a lower surface side of the sample support 2 to an upper surface side of the sample support 2 via the through-holes by a capillary phenomenon. The sample 10 stays on the upper surface side of the sample support 2 due to surface tension.

Subsequently, as illustrated in (c) of FIG. 1, an ultraviolet laser beam is applied to the upper surface side of the sample support 2, and thereby the sample 10 moved to the upper surface side of the sample support 2 is ionized and emitted into a vacuum. To be specific, energy of the ultraviolet laser beam is transmitted from the sample support 2 absorbing the energy to the sample 10 moved to the upper surface side of the sample support 2. The sample 10 obtaining the energy is evaporated and obtains electric charges to be sample ions (an ionized sample) 11. The sample ions 11 emitted into the air in this way are detected by a detector 3, and the detected sample ions 11 are measured. In this way, mass spectrometry of the sample 10 is performed.

The mass spectrometry method according to the present embodiment uses time-of-flight mass spectrometry (TOF-MS) by way of example. An outline of TOF-MS is shown below. In TOF-MS, a ground electrode (not shown) is provided between the sample support 2 and the detector 3, and a predetermined voltage is applied to the sample support 2. Thereby, a potential difference occurs between the sample support 2 and the ground electrode, and the sample ions 11 generated at the upper surface side of the sample support 2 are accelerated and moved toward the ground electrode by the potential difference. Afterward, the sample ions 11 fly in a drift space in which there are no electric and magnetic fields provided from the ground electrode to the detector 3, and finally reach the detector 3. Here, since the potential difference between the sample support 2 and the ground electrode is constant with respect to any of the sample ions 11, energy given to each of the sample ions 11 is constant. For this reason, the sample ions 11 having a smaller molecular weight fly in the drift space at a higher speed and reach the detector 3 within a shorter time. In TOF-MS, mass spectrometry is performed on the basis of differences in arrival time of the sample ions 11 at the detector 3.

Figure 2:
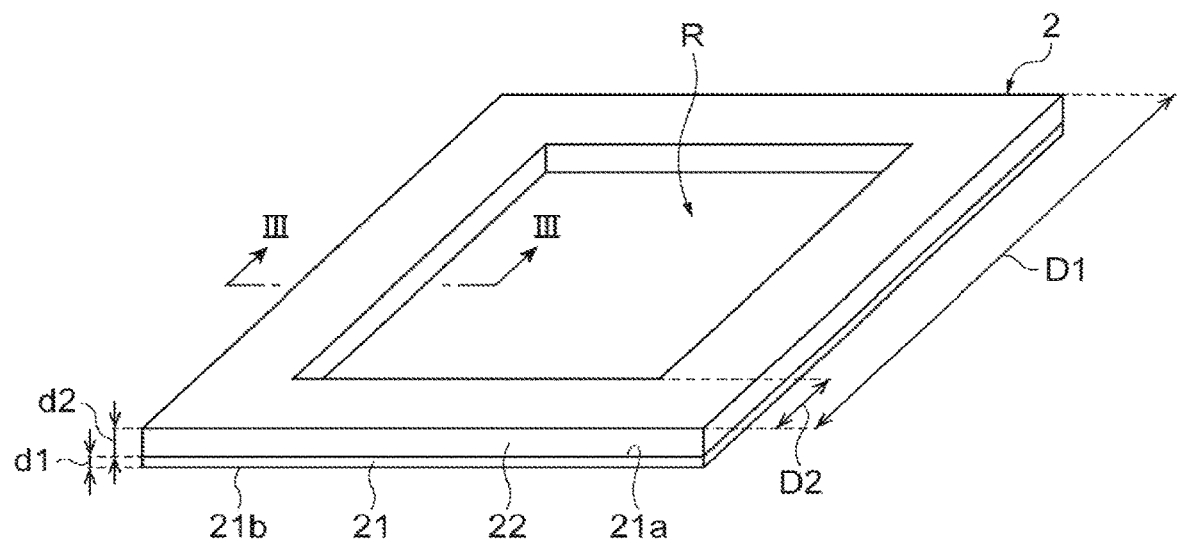
FIG. 2 is a perspective view of a sample support used in the mass spectrometry method according to the present embodiment.

Next, the sample support 2 will be described using FIGS. 2 to 5. FIG. 2 is a perspective view illustrating an external appearance of the sample support 2 (a substrate 21 and a frame 22). In practice, a plurality of through-holes S are provided in the substrate 21, and the sample support 2 is provided with a bonding layer G that bonds the substrate 21 and the frame 22, and a conductive layer 23 that covers surfaces of the substrate 21 and the frame 22 (including inner surfaces of the through-holes S). However, since these layers are extremely small with respect to the substrate 21 and the frame 22, these layers are not illustrated in FIG. 2. Meanwhile, in FIG. 3, which is a sectional view taken along line III-II of FIG. 2, the through-holes S, the conductive layer 23, and the bonding layer G are shown in dimensions larger than actual dimensions in order to describe arrangement configurations of the through-holes S, the conductive layer 23, and the bonding layer G.

Figure 3:
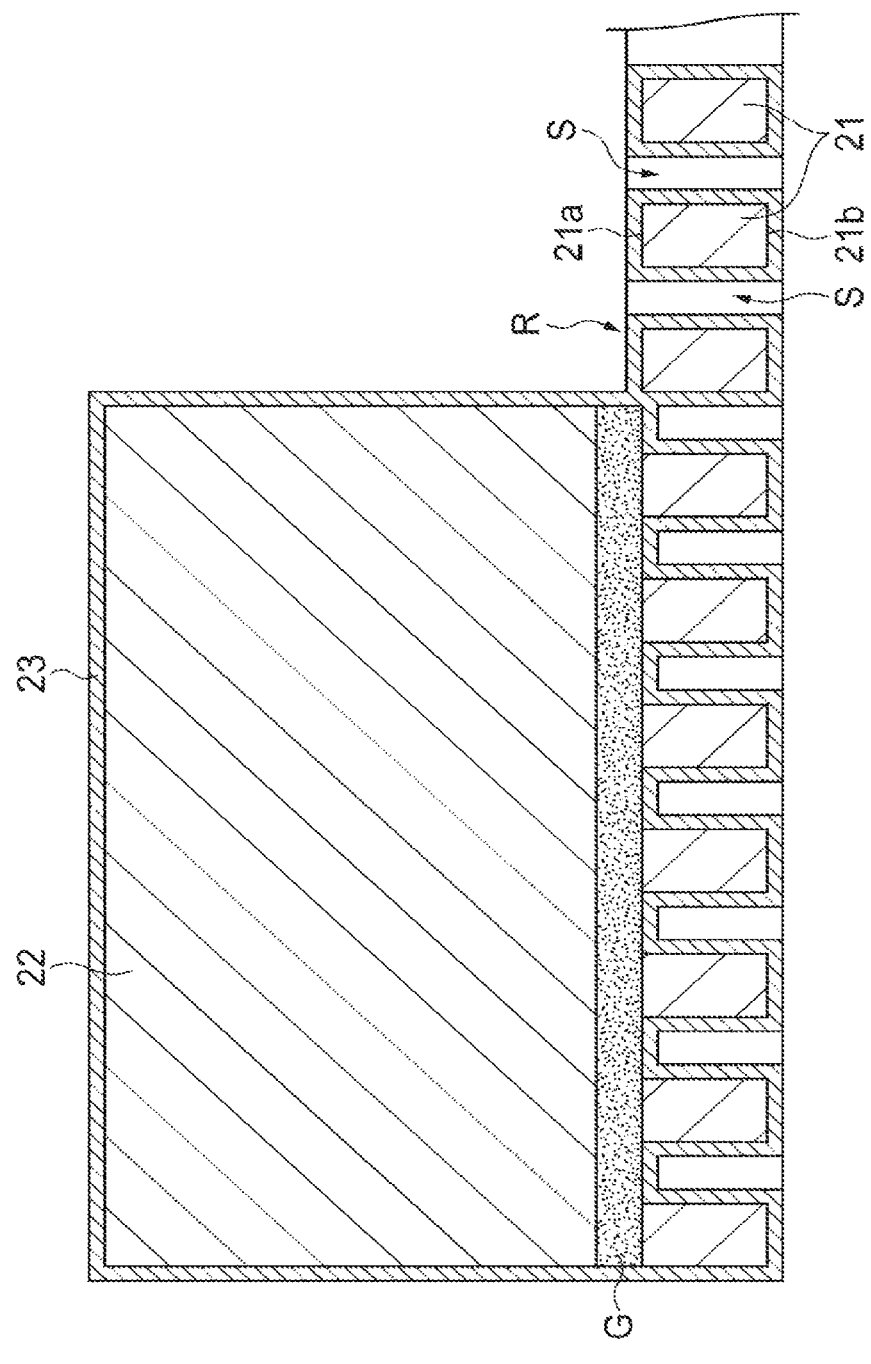
FIG. 3 is a sectional view taken along line III-III of FIG. 2.

As illustrated in FIGS. 2 and 3, the sample support 2 is a sample support for the SALDI method and has the rectangular plate-like substrate 21 in which the plurality of through-holes S are provided to pass from one surface 21a thereof to the other surface 21b thereof, and the frame 22 that is mounted on an outer edge of the one surface 21a of the substrate 21.

The one surface 21a and the other surface 21b of the substrate 21 have, for instance, square shapes in which a length D1 of one side thereof is 1 cm. A thickness d1 from the one surface 21a to the other surface 21b of the substrate 21 is 1 to 50 μm. In the present embodiment, the substrate 21 is formed of an insulating material by way of example. The substrate 21 is, for instance, an alumina porous film in which the plurality of through-holes S, each of which has a nearly constant hole diameter, are formed by anodizing aluminum (Al). The substrate 21 may be formed by anodizing a valve metal other than Al such as tantalum (Ta), niobium (Nb), titanium (Ti), hafnium (Hf), zirconium (Zr), zinc (Zn), tungsten (W), bismuth (Bi), antimony (Sb), or the like, or by anodizing silicon (Si).

The frame 22 is provided along the outer edge of the one surface 21a of the substrate 21 in a quadrilateral ring shape. A width D2 of the frame 22 is, for instance, 2 mm. A thickness d2 of the frame 22 is, for instance, 10 to 500 μm. An effective region R of the one surface 21a of the substrate 21 which is not covered with the frame 22 is a square region of 0.6 mm squared. The effective region R functions as a region for moving the sample 10 from the other surface 21b to the one surface 21a due to a capillary phenomenon (to be described below). The frame 22 is provided at an outer edge of the substrate 21, and thereby bending of the substrate 21 is suppressed. Since a portion at which the frame 22 is provided can be fixed or grasped, handling thereof is facilitated when the sample support 2 is supported or moved. In the present embodiment, the frame 22 is provided in the quadrilateral ring shape, but it may be provided along the outer edge of the substrate 21 in an annular shape. The frame 22 is provided in the annular shape, and thereby the bending of the substrate 21 is further suppressed than in a case in which the frame 22 is provided in the quadrilateral ring shape.

As illustrated in FIG. 3, the frame 22 is bonded to a surface (the one surface 21a) of the substrate 21 via the bonding layer G. As a material of the bonding layer G, a bonding material emitting a small amount of gas, such as low-melting-point glass, or an adhesive for a vacuum can be used. In the present embodiment, the frame 22 is bonded to the substrate 21 by overlapping a portion in which the through-holes S are provided in the one surface 21a of the substrate 21 by way of example. For this reason, the through-holes S allow bending of interfaces between the portion at which the frame 22 is provided and a portion at which the frame 22 is not provided in the substrate 21. Thereby, the substrate 21 is inhibited from being broken on the boundary surface.

The frame 22 has nearly the same coefficient of thermal expansion as the substrate 21. The frame 22 is, for instance, a ceramic member or the like having the same composition as the substrate 21. The frame 22 is formed of, for instance, glass or a metal. In this way, the coefficients of thermal expansion of the substrate 21 and the frame 22 approximate each other, and thereby deformation or the like (for instance, strains of the substrate 21 and the frame 22 during thermal expansion) caused by a change in temperature can be prevented.

Figure 5:
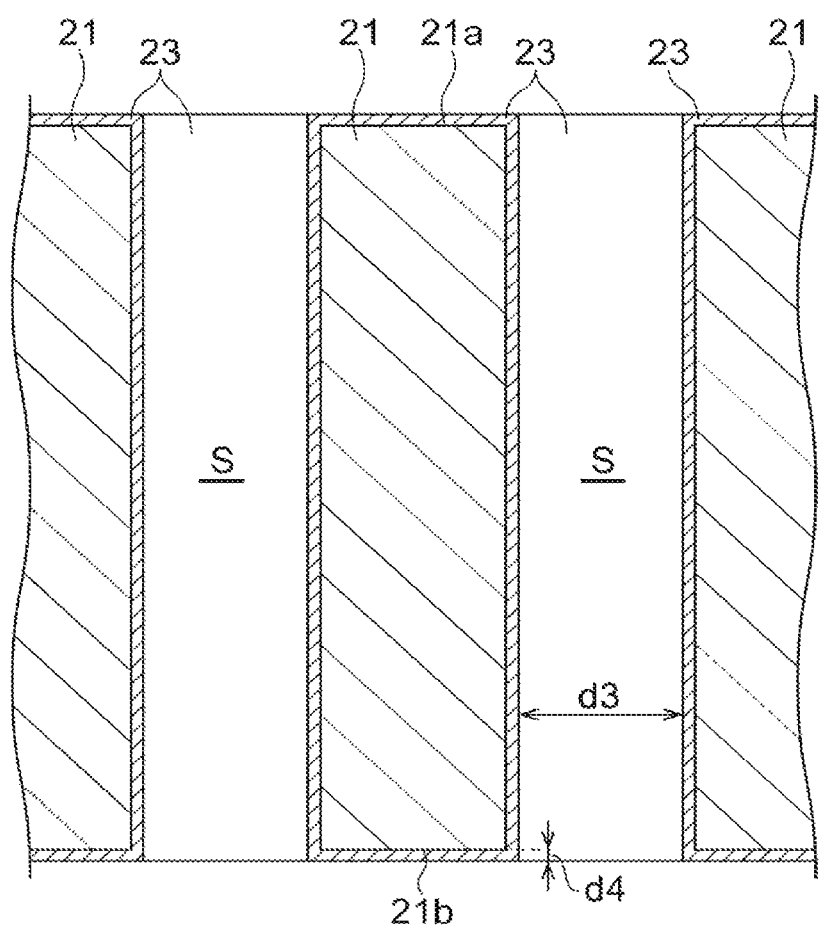
FIG. 5 is an enlarged sectional view of major parts of the sample support of FIG. 2.

As illustrated in FIGS. 3 and 5, the sample support 2 has the conductive layer 23 that covers the one surface 21a and the other surface 21b of the substrate 21, the inner surfaces of the through-holes S, and a surface of the frame 22. The conductive layer 23 is a layer formed of a conductive material provided to give conductivity to the insulating substrate 21. However, the conductive layer 23 is not hindered from being provided even when the substrate 21 is formed of a conductive material. As the material of the conductive layer 23, a metal having low affinity (reactivity) with the sample 10 and high conductivity is preferred due to reasons that will be mentioned below.

For example, when the conductive layer 23 is formed of a metal such as copper (Cu) having high affinity with the sample 10 such as a protein, the sample 10 may be ionized with Cu atoms attached to sample molecules in a process (to be described below) of ionizing the sample 10. That is, when a molecular weight of the sample ions 11 detected by the detector 3 is measured, the measured weight deviates from an actual molecular weight of the sample 10 by a mass of the attached Cu, and hence accurate measurement is not performed. Therefore, as the material of the conductive layer 23, a metal having low affinity with the sample 10 is preferred.

Meanwhile, a metal having high conductivity can give a constant voltage in an easy and stable way. For this reason, when a metal having high conductivity is used as the conductive layer 23, a constant voltage is easily applied to the substrate 21 in order to generate a constant potential difference between the aforementioned ground electrode and the substrate 21. In addition, since a metal having higher conductivity shows a tendency to have higher thermal conductivity, the energy of the laser beam applied to the substrate 21 can be efficiently transmitted to the sample 10 via the conductive layer 23. Therefore, as the material of the conductive layer 23, a metal having high conductivity is preferred.

From the above viewpoint, for example, gold (Au), platinum (Pt), or the like is used as the material of the conductive layer 23. For example, the conductive layer 23 can be formed by forming a film of Au or Pt on the one surface 21a and the other surface 21b of the substrate 21, the inner surfaces of the through-holes S, and the surface of the frame 22 using a plating method, an atomic layer deposition (ALD) method, a vapor deposition method, a sputtering method, or the like. In addition to Au and Pt, for example, chromium (Cr), nickel (Ni), titanium (Ti), etc. can be used as the material of the conductive layer 23.

Figure 4:
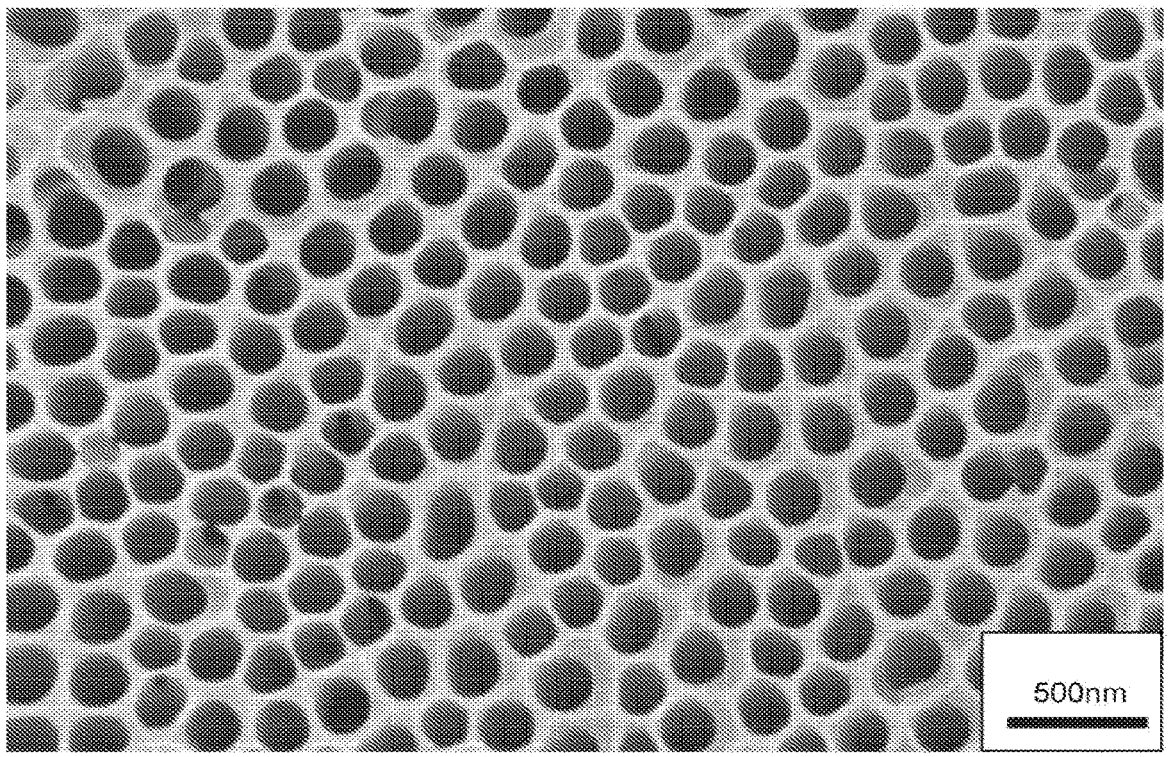
FIG. 4 is an enlarged plan view on an effective region R of the sample support of FIG. 2.

FIG. 4 is an enlarged plan view of the effective region R of the sample support 2. In FIG. 4, black portions denote the through-holes S, and white portions denote partition wall portions at which the through-holes S are not formed. As illustrated in FIG. 4, the plurality of through-holes S having approximately constant sizes are formed on the surface of the substrate 21. The plurality of through-holes S may be formed at such a size that the sample 10 can be moved (raised) from the other surface 21b to the one surface 21a by a capillary phenomenon (to be described below). As in the example of FIG. 4, the sizes of the through-holes S may be uneven, and portions at which the plurality of through-holes S are coupled to one another may be present. An aperture ratio of the through-holes S (an area of portions at which the through-holes S are formed/a whole area) in the effective region R ranges from 10% to 80% from a practical point of view, and particularly preferably ranges from 60% to 80%.

As illustrated in FIG. 5, the through-holes S extend from the one surface 21a side to the other surface 21b side of the substrate 21. A width d3 of each of the through-holes S is 1 to 700 nm. A thickness d4 of the conductive layer 23 is, for instance, about 1 to 25 nm. Here, the width d3 of each of the through-holes S is a hole width after the conductive layer 23 is formed in the through-holes S. When the substrate 21 having the through-holes S, each of which has a hole width of 1 to 700 nm, is used, the movement of the sample 10 caused by the aforementioned capillary phenomenon can be more smoothly performed. As in the present embodiment, when a sectional shape of each of the through-holes S is a nearly circular shape, the width d3 of each of the through-holes S refers to a diameter of each hole. Meanwhile, when the sectional shape of each of the through-holes S is not a circular shape, the width of each of the through-holes S refers to a diameter (an effective diameter) of an imaginary cylinder fitted into each of the through-holes S.

Figure 6:
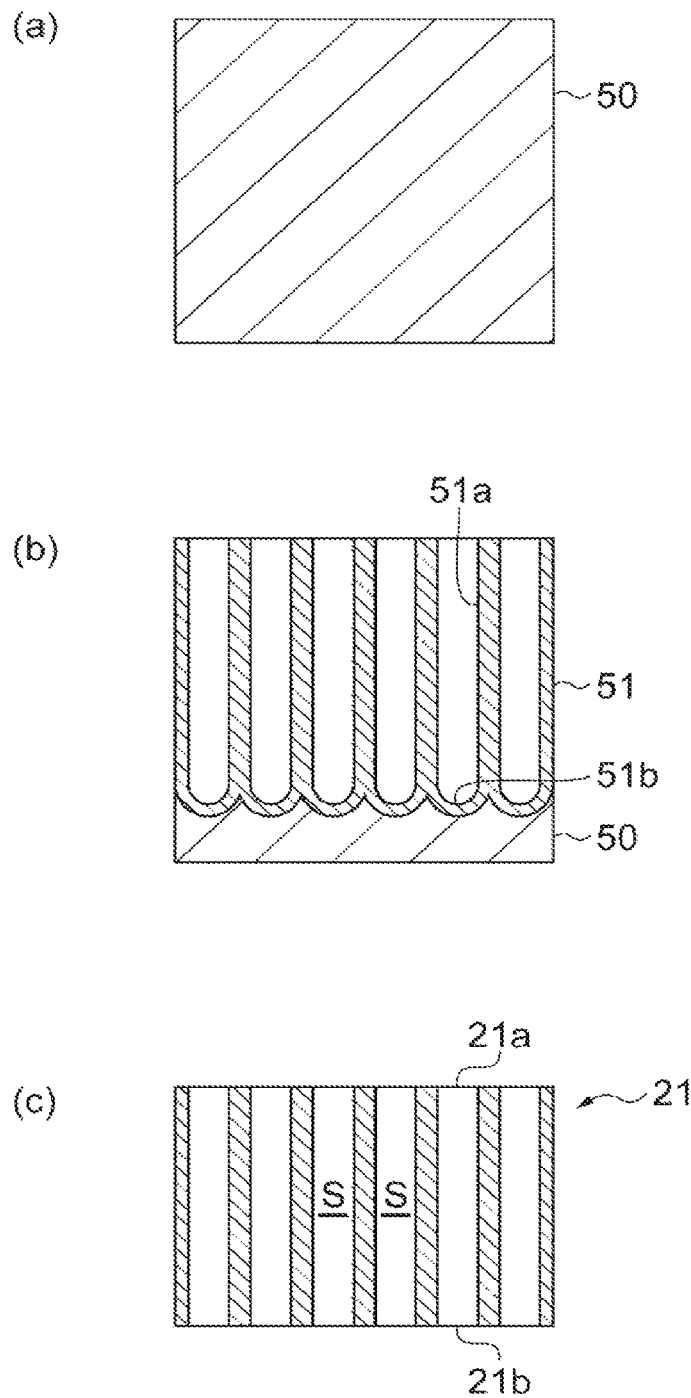
FIG. 6 is view illustrating a process of manufacturing a substrate of FIG. 2.

Next, a process of manufacturing the sample support 2 will be described using FIGS. 3 and 6. First, a process of manufacturing the substrate 21 will be described using FIG. 6. As illustrated in (a) of FIG. 6, an Al (Aluminum) substrate 50 that will become a material of the substrate 21 is prepared. Subsequently, as illustrated in (b) of FIG. 6, the Al substrate 50 is anodized. Thereby, the Al substrate 50 is oxidized from a surface thereof, and an anodized film 51 having a plurality of concavities 51a is formed. Subsequently, as illustrated in (c) of FIG. 6, the anodized film 51 is peeled from the Al substrate 50, and a bottom 51b of the anodized film 51 is removed or perforated. Thereby, the substrate 21 in which the plurality of through-holes S passing from one surface 21a to the other surface 21b thereof are provided is obtained.

After the substrate 21 is manufactured in this way, the frame 22 is mounted on an outer edge of the substrate 21 via the bonding layer G such as low-melting-point glass or an adhesive for a vacuum. Thereby, the thing which is in a state before the conductive layer 23 is formed in the sample support 2 illustrated in FIG. 3 is obtained. Finally, the conductive layer 23 formed of Au or Pt is provided to cover the one surface 21a and the other surface 21b of the substrate 21, the inner surfaces of the through-holes S, and the surface of the frame 22. As described above, the conductive layer 23 is formed by forming a film of Au or Pt on the one surface 21a and the other surface 21b of the substrate 21, the inner surfaces of the through-holes S, and the surface of the frame 22 using a plating method, an ALD method, or the like. Thereby, the sample support 2 illustrated in FIG. 3 is manufactured.

In the anodization of Al, the substrate 21 is adjusted to have the thickness d1 of 1 to 50 μm, and each of the through-holes S is adjusted to have the width d3 of 1 to 700 nm. To be specific, a thickness of the Al substrate 50 prepared first or conditions such as a temperature, a voltage, etc. in the anodization of the Al substrate 50 are properly set, and thereby the thickness d1 of the substrate 21 and the width d3 of each of the through-holes S are formed to have predetermined sizes (sizes included in the above range).

Figure 7:
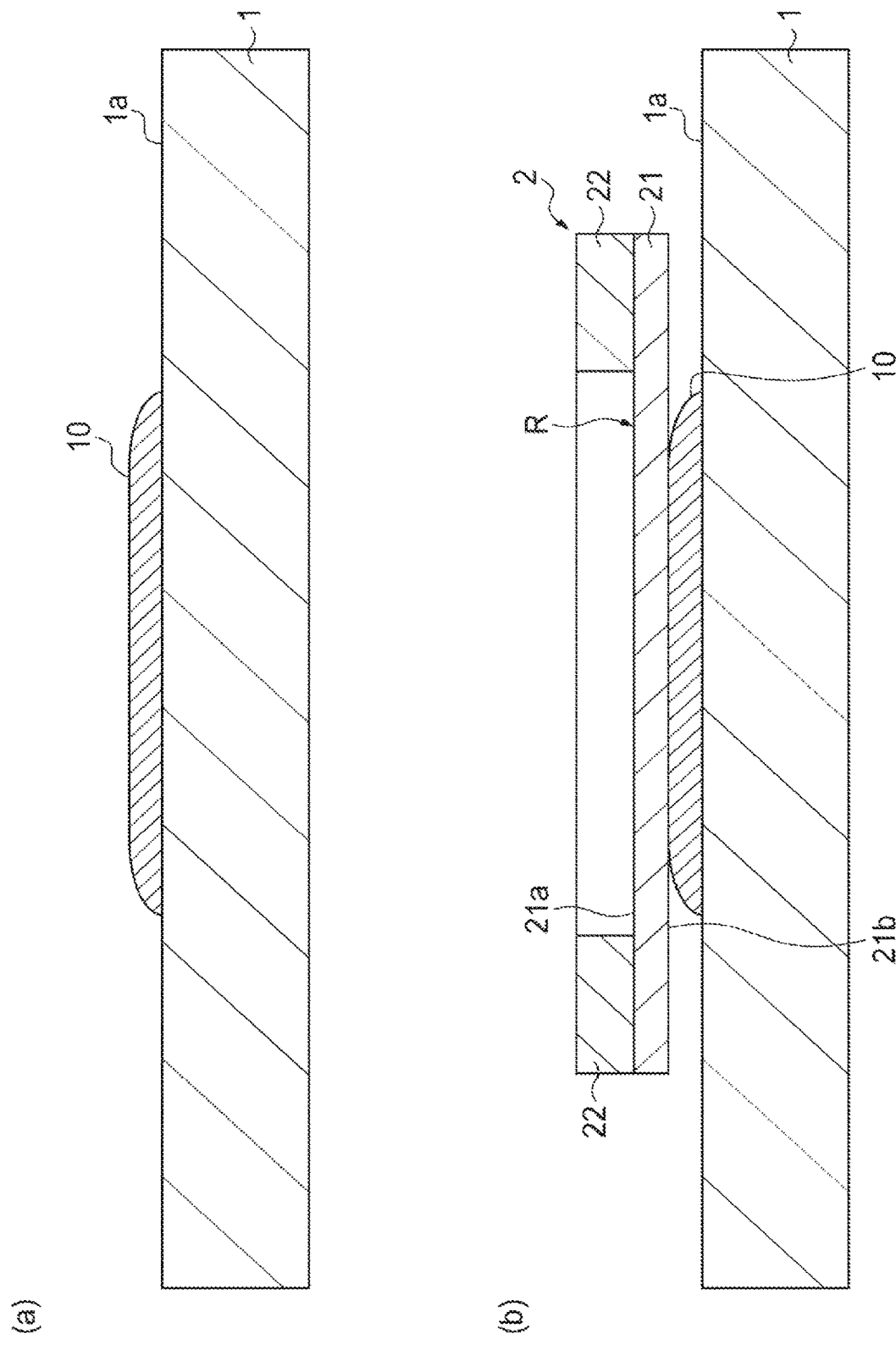
FIG. 7 is a view illustrating a procedure of the mass spectrometry method according to the present embodiment.
Figure 9:
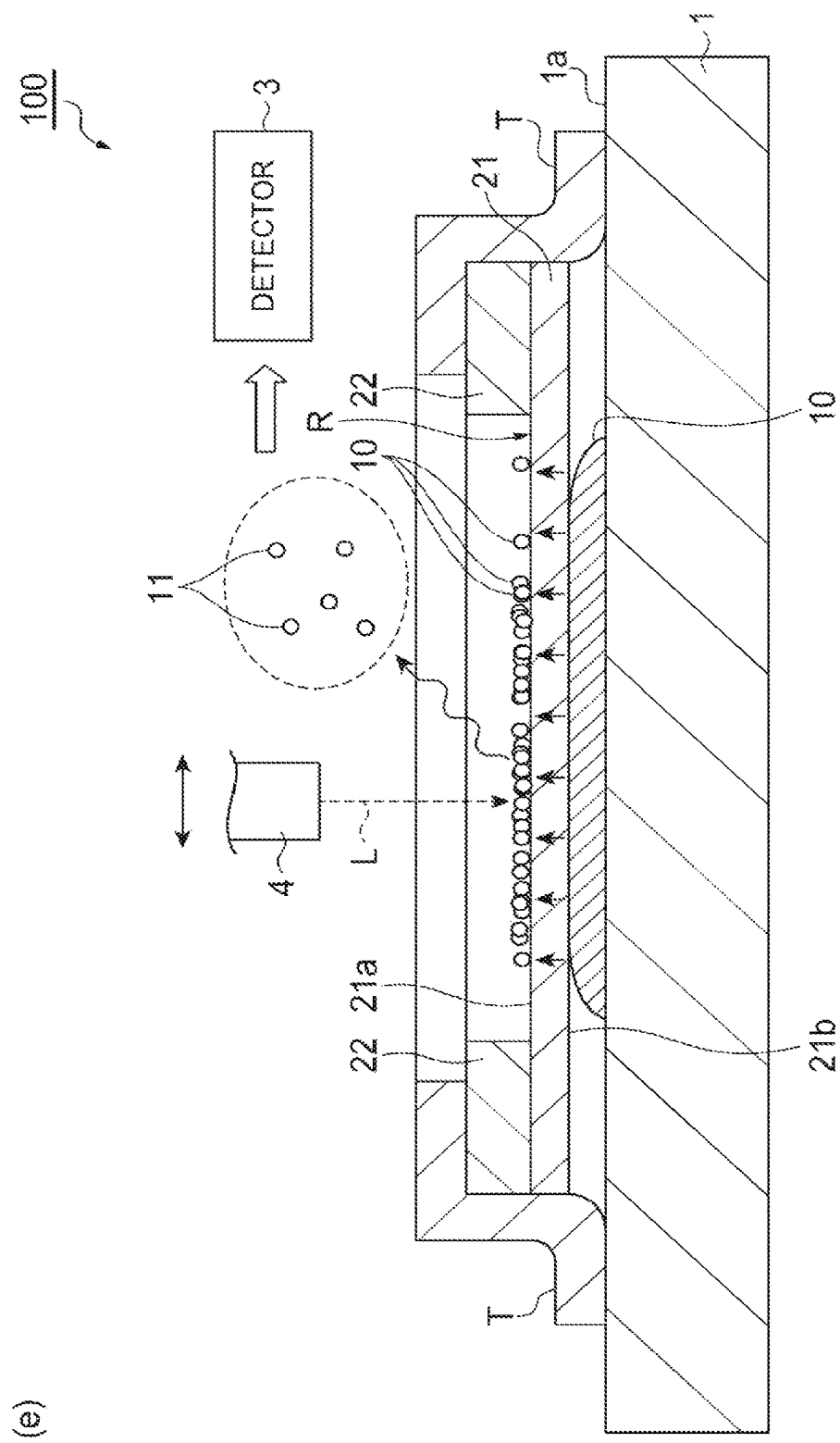
FIG. 9 is a view illustrating a procedure of the mass spectrometry method according to the present embodiment.
Figure 10:
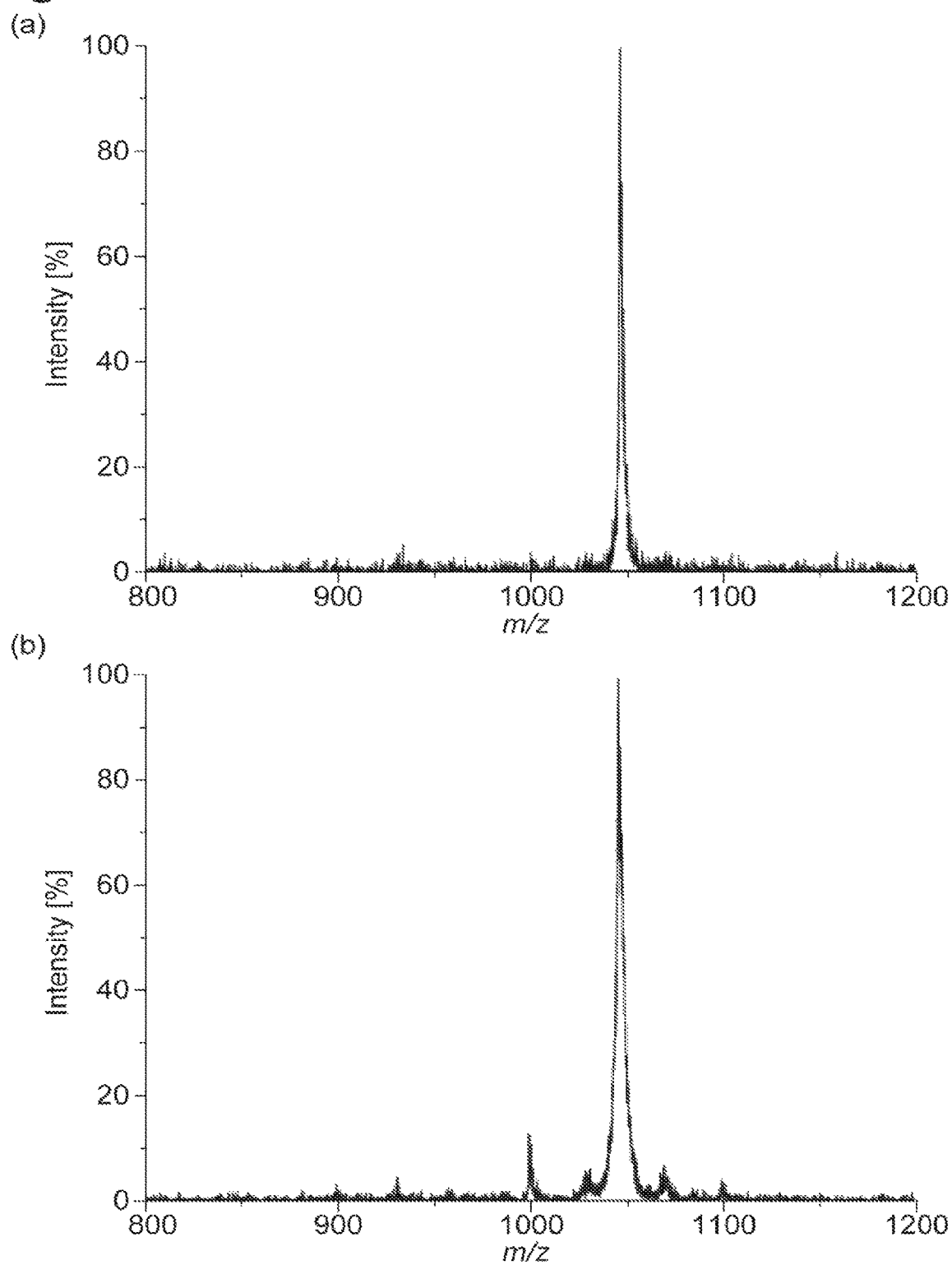
FIG. 10 is a view illustrating a relation between a hole width of a through-hole and a mass spectrum.
Figure 11:
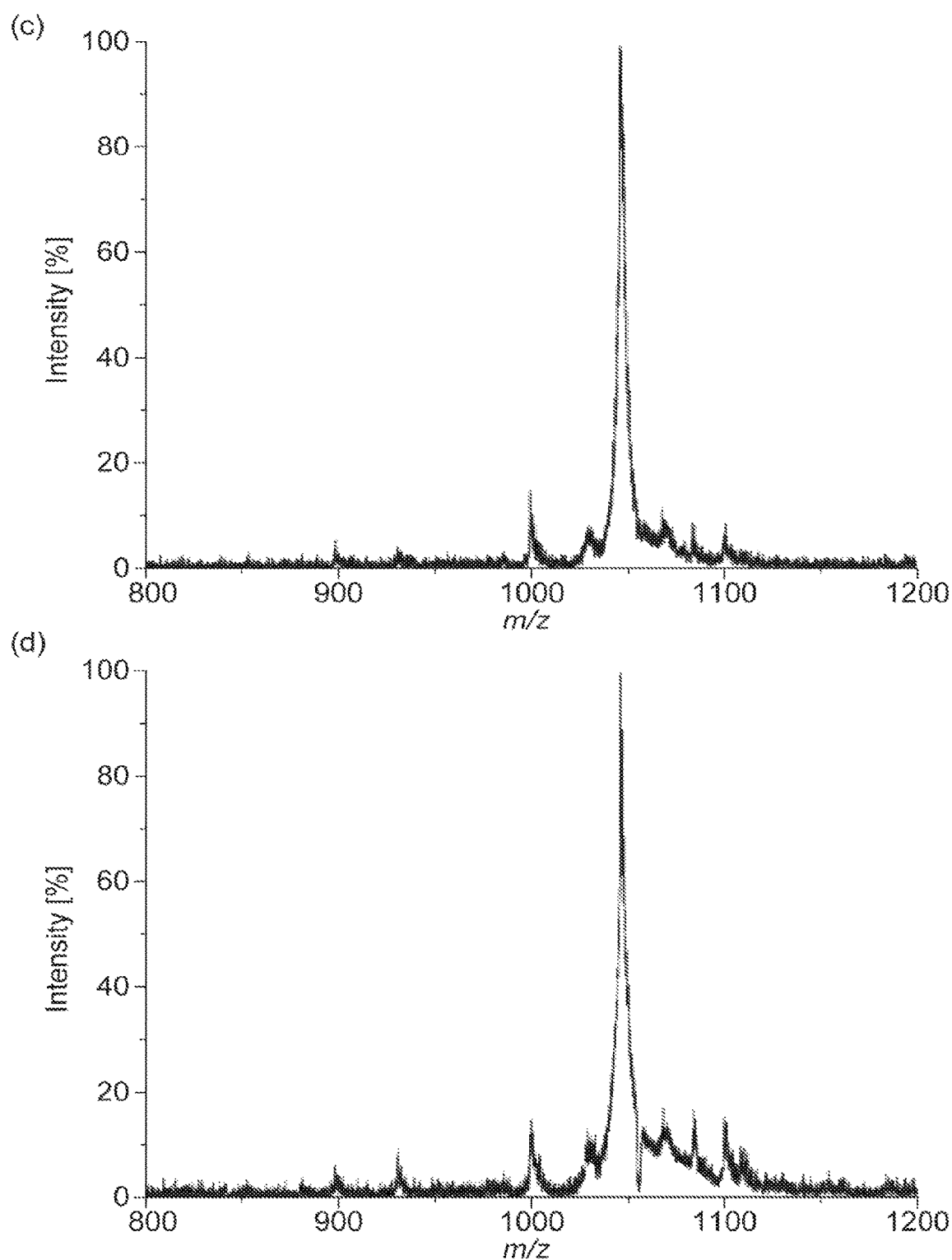
FIG. 11 is a view illustrating a relation between the hole width of the through-hole and the mass spectrum.
Figure 12:
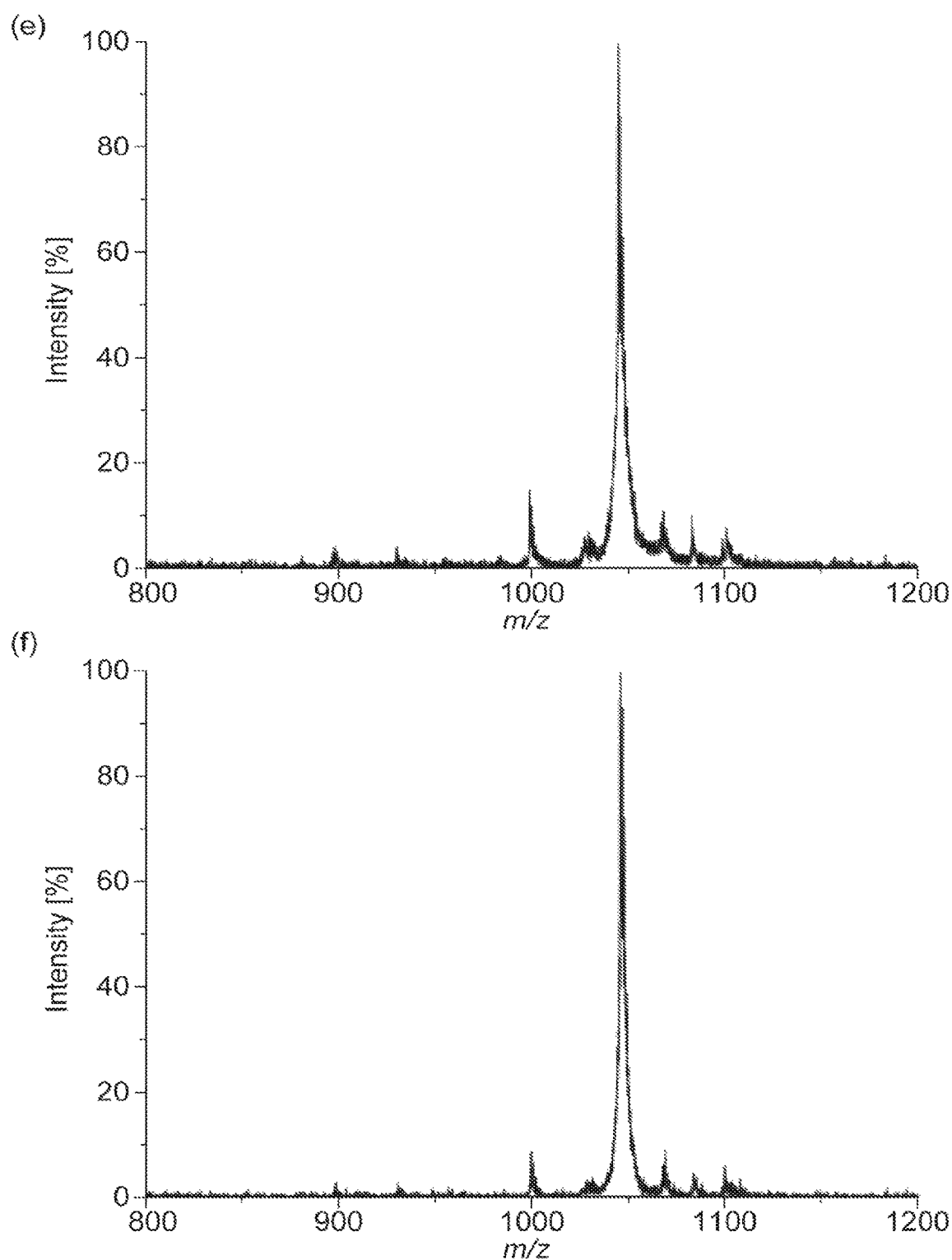
FIG. 12 is a view illustrating a relation between the hole width of the through-hole and the mass spectrum.

Next, a procedure of the mass spectrometry method using the sample support 2 will be described using FIGS. 7 to 9. In FIGS. 7 to 9, the conductive layer 23, the through-holes S, and the bonding layer G are not illustrated.

First, a mass spectrometry device 100 for performing mass spectrometry using the sample support 2 will be described using FIG. 9. The mass spectrometry device 100 comprises the sample stage 1 on which the sample 10 is placed, a laser beam application unit 4, and the detector (the detection unit) 3.

In a state in which the sample support 2 is arranged on the sample 10 placed on the sample stage 1, the laser beam application unit 4 applies a laser beam L to the one surface 21*a* while changing application positions thereof. Here, the sample support 2 is placed on the sample 10 such that the other surface 21*b* comes into contact with the sample 10 via the conductive layer 23. The laser beam L applied by the laser beam application unit 4 is, for instance, an ultraviolet laser beam such as a nitrogen laser beam (an $N_2$ laser beam) having a wavelength of 337 nm or the like.

The detector 3 detects the sample 10 (the sample ions 11), which is ionized by the laser beam L being applied from the laser beam application unit 4 at each application position. To be specific, the laser beam application unit 4 performs two-dimensional scanning on the effective region R of the sample support 2 according to a predetermined movement width and a predetermined moving direction, and applies the laser beam L at each scanning position. The detector 3 detects the sample ions 11 generated by the laser beam L being applied at each scanning position. Thereby, mass spectrometry can be performed at each position on the effective region R. Results of the mass spectrometry at each position of the sample 10 obtained in this way are synthesized, and thereby imaging mass spectrometry for imaging a two-dimensional distribution map of sample molecules can be performed. A procedure of the mass spectrometry performed by the mass spectrometry device 100 will be described below in detail using FIGS. 7 to 9.

First, the aforementioned sample support 2 is prepared (a first process). The sample support 2 may be prepared by a person who performs the mass spectrometry and manufactures the sample support 2 in person using the mass spectrometry device 100, or by acquiring the sample support 2 from a manufacturer, a seller, or the like of the sample support 2.

Subsequently, as illustrated in (a) of FIG. 7, the sample 10 to be subjected to mass spectrometry is placed on a placement surface 1*a* of the sample stage 1 and, as illustrated in (b) of FIG. 7, the sample support 2 is arranged on the sample 10 such that the other surface 21*b* comes into contact with the sample 10 via the conductive layer 23 (see FIG. 3) (a second process). Here, to move the sample 10 targeted on the spectrometry to the one surface 21*a* side of the substrate 21 according to a capillary phenomenon, the sample support 2 is arranged on the sample 10 such that the sample 10 is included within the effective region R in the planar view. To smooth the movement of the sample 10 caused by the capillary phenomenon (to be described below), a solution (for instance, an acetonitrile mixture or the like) for reducing viscosity of the sample 10 may be mixed with the sample 10.

Subsequently, as illustrated in (a) of FIG. 8, the sample support 2 is fixed to the sample stage 1 (a continuation of the second process). Here, as an example, four sides of the sample support 2 (upper and lateral surfaces of the frame 22 and lateral surfaces of the substrate 21) are fixed to the placement surface 1*a* of the sample stage 1 by an adhesive tape T having conductivity such as a carbon tape or the like. In this way, as the sample support 2 is fixed to the sample stage 1, the sample 10 and the sample support 2 are brought into close contact with each other, and the movement of the sample 10 caused by the capillary phenomenon (to be described below) can be more smoothly performed. Side-slippage of the sample support 2 arranged on the sample 10 can be prevented, and a loss of positional information of the sample 10 due to the sideslip of the sample support 2 can be suppressed.

Here, when the sample stage 1 has conductivity, the sample stage 1 and the sample support 2 are electrically connected by the adhesive tape T having conductivity. Therefore, a predetermined current is applied to the sample stage 1 in the state in which the sample support 2 is fixed to the sample stage 1 by the adhesive tape T as illustrated in (a) of FIG. 8, and thereby a predetermined voltage is applied to the substrate 21. Thereby, a constant potential difference can be generated between the aforementioned ground electrode and the substrate 21. In the present embodiment, since the conductive layer 23 covers the frame 22 and the adhesive tape T is in contact with the conductive layer 23 on the frame 22, the sample support 2 and a power source (a predetermined power source that applies the current to the sample stage 1) can be brought into contact with each other on the frame 22. That is, the sample support 2 and the power source can be brought into contact with each other without reducing the effective region R on the substrate 21.

As illustrated in (b) of FIG. 8, as described above, the sample support 2 is arranged on the sample 10, and thereby the sample 10 is moved (raised) from the other surface 21*b* side of the substrate 21 toward the one surface 21*a* side via the through-holes S by the capillary phenomenon. The sample 10 enters a state in which it stays on the one surface 21*a* side of the sample support 2 due to surface tension. Here, the placement surface 1*a* of the sample stage 1 and the one surface 21*a* and the other surface 21*b* of the substrate 21 are arranged to be nearly parallel to each other. Therefore, the sample 10 placed on the sample stage 1 is moved from the other surface 21*b* side to the one surface 21*a* side of the substrate 21 via the through-holes S in a direction perpendicular to the placement surface 1*a* of the sample stage 1 due to the capillary phenomenon. Thereby, before and after the movement caused by the capillary phenomenon, the positional information of the sample 10 (each sample molecule composing the sample 10) is maintained. In other words, two-dimensional coordinates (positions on a two-dimensional plane parallel to the placement surface 1*a* of the sample stage 1) of each sample molecule composing the sample 10 are not greatly changed before and after the movement caused by the capillary phenomenon. Accordingly, due to this capillary phenomenon, the sample 10 can be moved from the other surface 21*b* side to the one surface 21*a* side of the substrate 21 while the positional information of the sample 10 is maintained.

Subsequently, as illustrated in FIG. 9, the laser beam L is applied to the one surface 21*a* of the substrate 21 by the laser beam application unit 4, and the sample 10 moved from the other surface 21*b* side to the one surface 21*a* side via the through-holes S by the capillary phenomenon is ionized (a third process). The ionized sample 10 (the sample ions 11) is detected by the detector 3 (a fourth process). While changing application positions of the laser beam L, the application of the laser beam L in the third process and the detection of the sample ions 11 in the fourth process are performed at each application position. To be specific, the laser beam application unit 4 scans the effective region R according to a predetermined movement width and a predetermined moving direction, and applies the laser beam L at each application position while changing the application positions of the laser beam L. The detector 3 detects the sample ions 11 emitted into a vacuum by applying the laser beam L from the laser beam application unit 4 at each application position. As a result, imaging mass spectrometry for imaging a two-dimensional distribution map of sample molecules can be performed on the basis of measurement results of the sample ions 11 detected at each application position.

According to the SALDI method (the first to third processes), the substrate 21 in which the plurality of through-holes S are provided is arranged on the sample 10, and thereby the sample 10 can be raised from the other surface 21b side toward the one surface 21a side of the substrate 21 via the through-holes S due to a capillary phenomenon. Thereby, the sample 10 can be moved from the other surface 21b side to the one surface 21a side of the substrate 21 while the positional information of the sample 10 (the two-dimensional distribution of the molecules composing the sample 10) is maintained. The laser beam L is applied to the one surface 21a of the substrate 21, and energy is transmitted to the sample 10 moved to the one surface 21a side via the conductive layer 23. Thereby, the sample 10 is ionized. As a result, the sample 10 can be ionized while the positional information of the sample 10 is maintained. Therefore, according to the aforementioned method, the sample 10 can be ionized by a simple operation in which the substrate 21, in which the plurality of through-holes S are provided, is placed on the sample 10 while the positional information of the sample 10 is maintained.

Al is anodized, and thereby the sample support 2 having the substrate 21 in which the plurality of through-holes S are provided is used. Thereby, the movement of the sample 10 caused by the aforementioned capillary phenomenon can be properly realized. Here, even when the sample support 2 having the substrate 21 obtained by anodizing a valve metal other than Al or Si instead of Al is used, the same effects are obtained.

The substrate 21 having the through-holes S, each of which has the hole width d3 of 1 to 700 nm, is used, and thereby the movement of the sample 10 caused by the aforementioned capillary phenomenon can be more smoothly performed.

Since the sample support 2 has the frame 22 mounted on the outer edge of the one surface 21a of the substrate 21, the bending of the substrate 21 is suppressed by the frame 22, and the sample support 2 is easily handled when supported or moved. For this reason, the arrangement of the sample support 2 on the sample 10 in the second process can be easily performed.

According to the mass spectrometry method (the first to fourth processes), the sample 10 can be ionized by a simple operation in which the sample support 2 is arranged on the sample 10 while the positional information of the sample 10 is maintained. While changing the application positions of the laser beam L, the ionized sample 10 (the sample ions 11) is detected at each application position, and thereby the two-dimensional distribution of the sample molecules can be perceived. Therefore, according to the mass spectrometry method, the imaging mass spectrometry for imaging the two-dimensional distribution map of the sample molecules can be performed by the simple operation.

According to the mass spectrometry device 100, the sample 10 can be ionized by a simple operation in which the sample support 2 is arranged on the sample 10 while the positional information of the sample 10 is maintained. The laser beam application unit 4 applies the laser beam L while changing the application positions, and the detector 3 detects the ionized sample 10 (the sample ions 11) at each application position, and thereby the two-dimensional distribution of the sample molecules can be perceived. Therefore, according to the mass spectrometry device 100, imaging mass spectrometry for imaging a two-dimensional distribution map of sample molecules can be performed by the simple operation.

While the embodiment of the present invention has been described, the present invention is not limited to the embodiment and can be modified in various ways without departing from the gist thereof.

For example, the substrate 21 may be formed of a conductive material such as a semiconductor. In this case, the sample support 2 can omit the conductive layer 23 for giving conductivity to the substrate 21. When the sample support 2 is not provided with the conductive layer 23, the sample support 2 is arranged on the sample 10 such that the other surface 21b comes into direct contact with the sample 10 in the second process. Even when the substrate 21 is formed of a conductive material in this way and the sample support 2 from which the conductive layer 23 is omitted is used, the same effects as when the sample support 2 having the aforementioned conductive layer 23 is used can be obtained.

The ionization of the sample 10 caused by the SALDI method (the first to third processes) can also be used for other measurements and experiments such as ion mobility measurement as well as the imaging mass spectrometry of the sample 10 which is described in the present embodiment.

The conductive layer 23 may be provided by vapor deposition or the like to cover at least the one surface 21a of the substrate 21. That is, the conductive layer 23 may not be provided on the other surface 21b of the substrate 21 and the inner surfaces of the through-holes S. In this case, the sample support 2 is arranged on the sample 10 such that the other surface 21b faces the sample 10 in the second process, and the other surface 21b comes into direct contact with the sample 10. If the conductive layer 23 is provided to cover the surface of the frame 22 and at least the one surface 21a of the substrate 21, the contact between the substrate 21 and the electrode can be made on the frame 22.

FIGS. 10 to 13 illustrate a relation between the hole width of each of the through-holes S and a mass spectrum measured by the mass spectrometry method. Here, as the sample support, a sample support in which the conductive layer 23 (here, Pt) is provided to cover the one surface 21a and the surface of the frame 22 without being provided on the other surface 21b of the substrate 21 and the inner surfaces of the through-holes S is used. The thickness d1 of the substrate 21 is 10 μm, and the sample to be measured is a peptide of "mass-to-charge ratio (m/z)=1049." In FIGS. 10 to 13, (a) shows measured results when the hole widths of the through-holes S are set to 50 nm, (b) shows measured results when the hole widths of the through-holes S are set to 100 nm, (c) shows measured results when the hole widths of the through-holes S are set to 200 nm, (d) shows measured results when the hole widths of the through-holes S are set to 300 nm, (e) shows measured results when the hole widths of the through-holes S are set to 400 nm, (f) shows measured results when the hole widths of the through-holes S are set to 500 nm, (g) shows measured results when the hole widths of the through-holes S are set to 600 nm, and (h) shows measured results when the hole widths of the through-holes S are set to 700 nm. In FIGS. 10 to 13, the longitudinal axis denotes signal intensity (Intensity) standardized as 100(%) for a peak value.

As illustrated in FIGS. 10 to 13, even when the hole widths of the through-holes S of the substrate 21 are any one of 50 nm, 100 nm, 200 nm, 300 nm, 400 nm, 500 nm, 600 nm, and 700 nm, a proper spectrum in which a peak can be observed is obtained. In this way, the sample support having the substrate 21 in which the conductive layer 23 is provided on at least the one surface 21a is used, and thereby the mass spectrometry can be properly performed.

Figure 14:
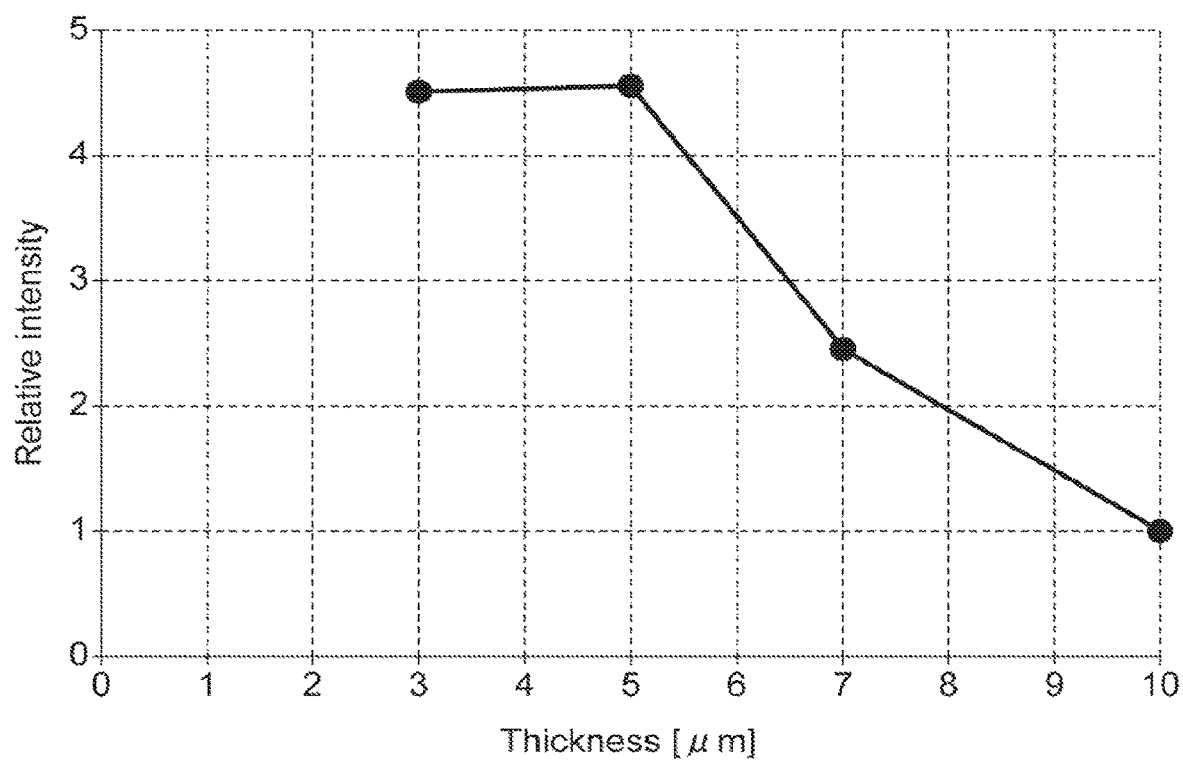
FIG. 14 is a view illustrating a relation between a thickness of a substrate and signal intensity.

FIG. 14 illustrates a relation between the thickness d1 (Thickness) of the substrate 21 and signal intensity of a peak measured by the mass spectrometry method. In FIG. 14, the longitudinal axis denotes relative signal intensity (Relative intensity) of the case the signal intensity is set to "1" when the thickness d1 of the substrate 21 is 10 μm. Here, as the sample support, a sample support in which the conductive layer 23 (here, Pt) is provided to cover the one surface 21a and the surface of the frame 22 without being provided on the other surface 21b of the substrate 21 and the inner surfaces of the through-holes S is used. The hole widths of the through-holes S are 200 nm. The sample to be measured is a peptide of "mass-to-charge ratio (m/z)=1049".

In the measured results, the signal intensity when the thickness d1 of the substrate 21 is 10 μm is of sufficient magnitude for mass spectrometry. As illustrated in FIG. 14, as the thickness d1 of the substrate 21 becomes smaller, the signal intensity shows a tendency to increase. When the thickness d1 of the substrate 21 ranges from 3 to 10 μm, sufficient signal intensity is obtained. Meanwhile, in terms of securing strength of the substrate, the thickness d1 of the substrate 21 is preferably large. For this reason, the thickness d1 of the substrate 21 may be set to 5 to 10 μm. Thereby, the strength of the substrate 21 can be maintained, and sufficient signal intensity can be obtained in the mass spectrometry.

Figure 15:
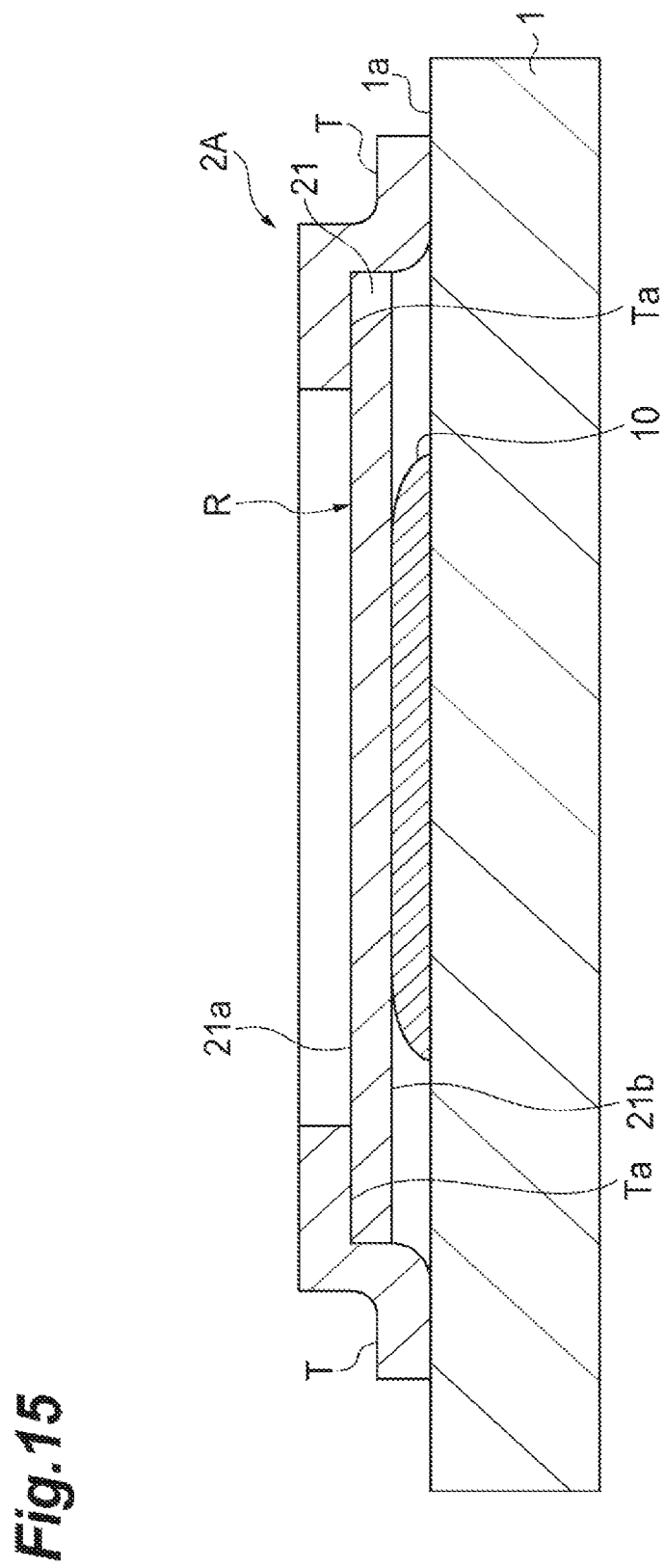
FIG. 15 is a view illustrating a first modification of the sample support.
Figure 16:
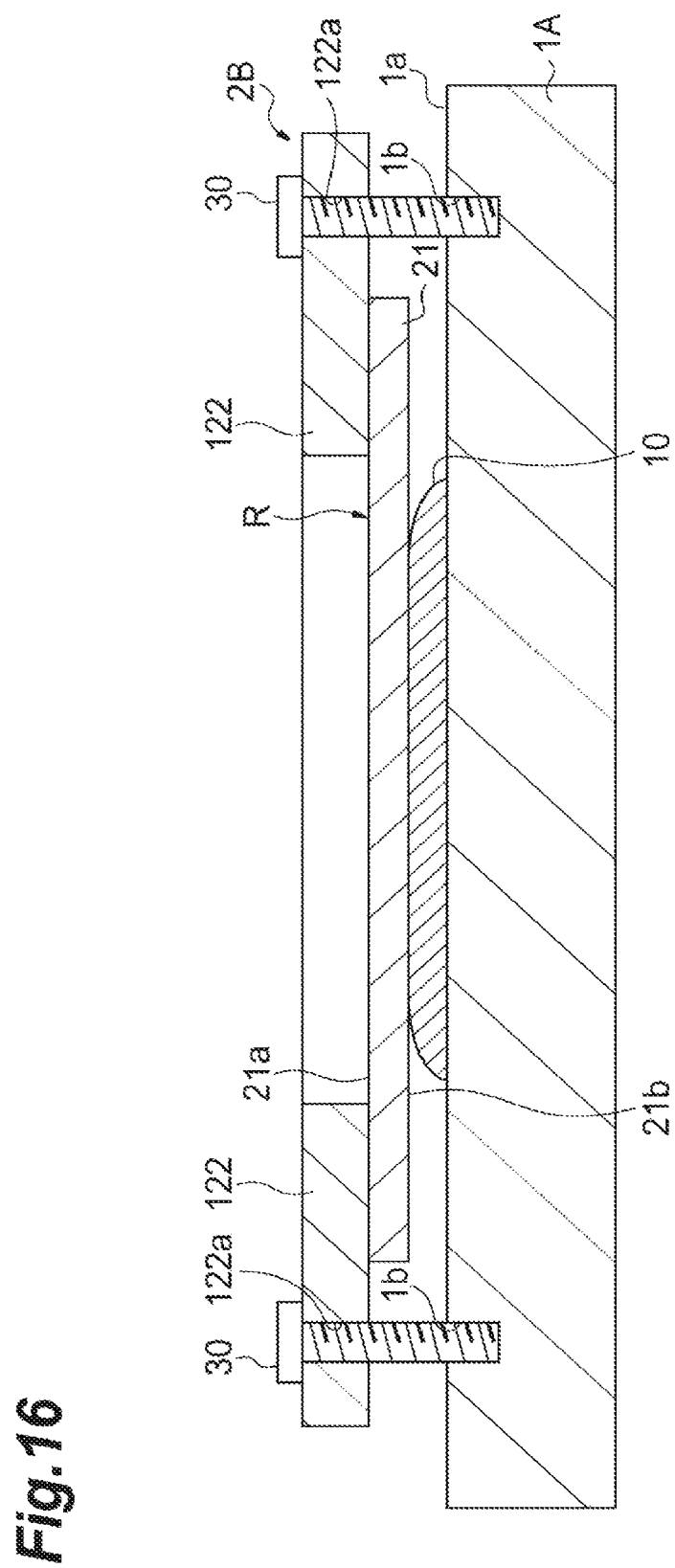
FIG. 16 is a view illustrating a second modification of the sample support.
Figure 17:
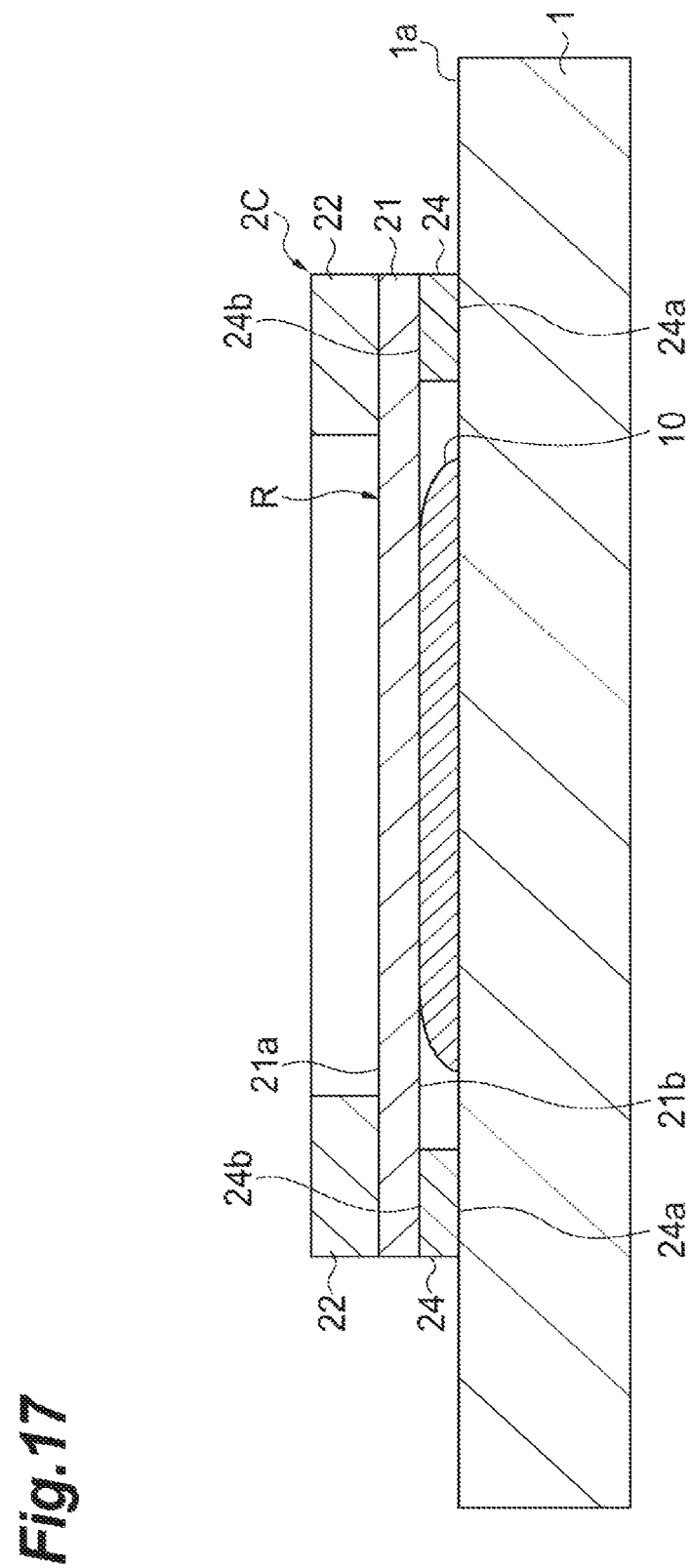
FIG. 17 is a view illustrating a third modification of the sample support.

In the embodiment, the form in which the frame 22 of the sample support 2 is fixed to the sample stage 1 by the adhesive tape T has been described, but a form of fixing the sample support 2 to the sample stage 1 is not limited to the form. Hereinafter, a variation of the form of fixing the sample support 2 to the sample stage 1 will be described using FIGS. 15 to 17 along with first to third modifications of the sample support 2. In FIGS. 15 to 17, the conductive layer 23 and the through-holes S are not illustrated. In FIGS. 16 and 17, the bonding layer G for bonding the frame and the substrate is also not illustrated.

(First Modification)

As illustrated in FIG. 15, a sample support 2A according to a first modification is mainly different from the sample support 2 in that a frame 22 is not provided for a substrate 21 and an adhesive tape T is directly stuck on one surface 21a of the substrate 21. The adhesive tape T is stuck on an outer edge of the one surface 21a such that an adhesive face Ta thereof faces the one surface 21a of the substrate 21, and the adhesive tape T has a portion that extends beyond an outer edge of the substrate 21. Thereby, as illustrated in FIG. 15, the adhesive face Ta can be stuck on the outer edge of the substrate 21 and a placement surface 1a of a sample stage 1. As a result, the sample support 2A is fixed to the sample stage 1 by the adhesive tape T. According to the sample support 2A, for example when mass spectrometry of a sample 10 whose surface has concavities and convexities is performed, a follow-up characteristic of the substrate 21 for the sample 10 can be improved.

When the sample stage 1 has conductivity, the sample stage 1 and the sample support 2A (particularly, a conductive layer 23 provided on the one surface 21a of the substrate 21) are electrically connected via the adhesive tape T having conductivity. Therefore, as illustrated in FIG. 15, in the state in which the sample support 2 is fixed to the sample stage 1 via the adhesive tape T, a predetermined current is applied to the sample stage 1, and thereby a predetermined voltage can be applied to the substrate 21.

The sample support 2A may be distributed in a state in which the adhesive tape T is stuck on the outer edge of the substrate 21 and an adhesive protection sheet is provided on the adhesive face Ta of the portion that extends beyond the outer edge of the substrate 21. In this case, a user of the sample support 2A releases the adhesive protection sheet immediately before the sample support 2A is fixed to the sample stage 1, and sticks the adhesive face Ta on the placement surface 1a, and thereby preparation of the mass spectrometry of the sample 10 can be easily performed.

(Second Modification)

As illustrated in FIG. 16, a sample support 2B according to a second modification is mainly different from the sample support 2 in that a frame 122 having a portion that extends beyond an outer edge of a substrate 21 is provided. When the sample support 2B is carried by this frame 122, damage to an end of the substrate 21 can be properly suppressed. Further, as illustrated in FIG. 16, insertion holes 122a for inserting screws 30 are provided in the portion of the frame 122 which extends beyond the outer edge of the substrate 21. In this case, for example when a sample stage 1A having screw holes 1b at positions corresponding to the insertion holes 122a is used, the sample support 2B can be reliably fixed to the sample stage 1A by screwing. To be specific, the screws 30 are inserted into the insertion holes 122a and the screw holes 1b, and thereby the sample support 2B can be fixed to the sample stage 1A.

When the sample stage 1A has conductivity and when the screws 30 have conductivity, the sample stage 1A and the sample support 2B (particularly, a conductive layer 23 formed on the frame 122) are electrically connected via the screws 30. Therefore, as illustrated in FIG. 16, in a state in which the sample support 2B is fixed to the sample stage 1A via the screws 30, a predetermined current is applied to the sample stage 1A, and thereby a predetermined voltage can be applied to the substrate 21.

(Third Modification)

As illustrated in FIG. 17, a sample support 2C according to a third modification is mainly different from the sample support 2 in that an adhesion layer 24 having one adhesive face 24a facing a direction directed from one surface 21a to the other surface 21b is provided at an outer edge of the other surface 21b of a substrate 21. The adhesion layer 24 is, for instance, a double-sided tape or the like that has a thickness predetermined depending on a thickness of a sample 10 to be measured. For example, the other adhesive face 24b of the adhesion layer 24 is previously stuck on the outer edge of the other surface 21b of the substrate 21, and the one adhesive face 24a of the adhesion layer 24 is stuck on a placement surface 1a when the sample support 2C is fixed to a sample stage 1. According to the sample support 2C, a configuration in which the sample support 2C is fixed to the sample stage 1 can be simplified.

When the sample stage 1 has conductivity and when the adhesion layer 24 has conductivity, the sample stage 1 and the sample support 2C (particularly, the substrate 21) are electrically connected via the adhesion layer 24. Therefore, as illustrated in FIG. 17, in a state in which the sample support 2C is fixed to the sample stage 1 via the adhesion layer 24, a predetermined current is applied to the sample stage 1, and thereby a predetermined voltage can be applied to the substrate 21.

The sample support 2C may be distributed in a state in which the adhesive face 24b of the adhesion layer 24 is stuck on the outer edge of the other surface 21b of the substrate 21 and an adhesive protection sheet is provided for the adhesive face 24a. In this case, a user of the sample support 2C releases the adhesive protection sheet immediately before the sample support 2C is fixed to the sample stage 1, and sticks the adhesive face 24a on the placement surface 1a, and thereby preparation of the mass spectrometry of the sample 10 can be easily performed.

The sample supports 2, 2A, 2B, and 2C according to the embodiment and the modifications may be baked after the conductive layer 23 is formed. The process of manufacturing a sample support in the embodiment may include a baking process of baking the sample support after the conductive layer 23 is formed. When the frame 22 is provided, the baking process is performed on a sample support having the substrate 21, the frame 22, and the conductive layer 23. When the frame 22 is omitted, the baking process is performed on a sample support having the substrate 21 and the conductive layer 23.

By performing this baking process, crystallinity of the conductive layer 23 (for instance, Pt) can be improved, and a sample support that is more suitable for mass spectrometry can be obtained. Here, the baking of the sample support is preferably performed such that a diffraction peak of a crystal of a conductive material (here, Pt) forming the conductive layer 23 is shown in an X-ray diffraction (XRD) measurement for the conductive layer 23 (the sample support) after the baking. Here, the expression of the "diffraction peak of the crystal of the conductive material is shown" means that a diffraction pattern (peak intensity or the like) of the crystal of the conductive material is more clearly shown than measured results obtained by the XRD measurement for the sample support before the baking.

Figure 18:
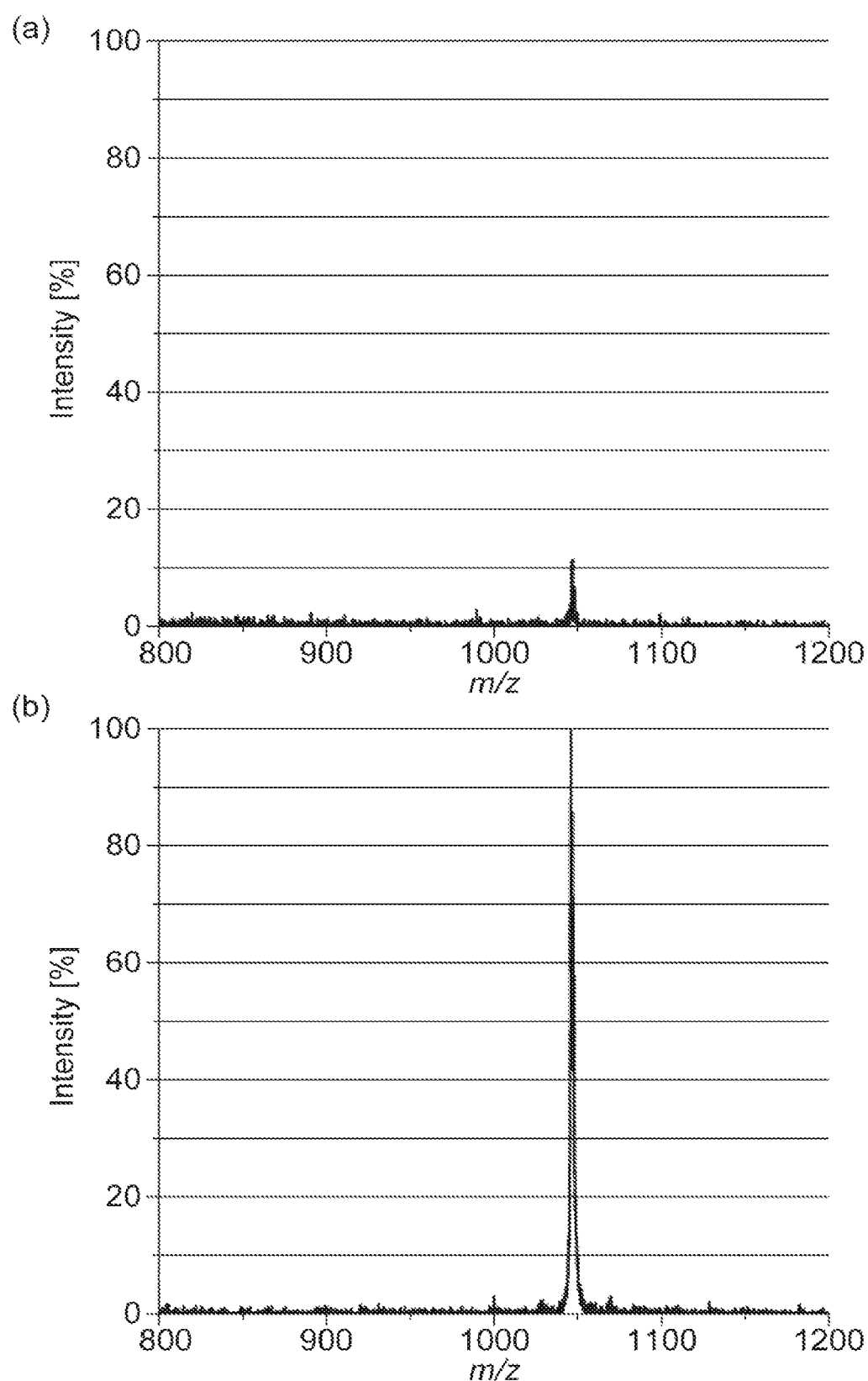
FIG. 18 is a view illustrating a mass spectrum according to mass spectrometry using a sample support before being baked and a mass spectrum according to mass spectrometry using a sample support after being baked.

(a) of FIG. 18 illustrates a mass spectrum measured by the mass spectrometry device 100 having the sample support before being baked. On the other hand, (b) of FIG. 18 illustrates a mass spectrum measured by the mass spectrometry device 100 having the sample support after being baked at a baking temperature of 400° C. Measurement conditions (a type of sample, a configuration of the sample support, etc.) other than the presence and absence of the baking are the same between (a) and (b) of FIG. 18. The longitudinal axes of (a) and (b) of FIG. 18 denote relative signal intensity of the case signal intensity of a peak (that is, a peak value of the graph in (b) of FIG. 18) is set to "100" when the sample support after the baking is used. As illustrated in FIG. 18, the signal intensity can be further improved in mass spectrometry by using the sample support after the baking than when using the sample support before the baking. In this way, a sample support that is more suitable for the mass spectrometry can be obtained by performing the baking process.

REFERENCE SIGNS LIST

1 Sample stage
2, 2A, 2B, 2C Sample support
3 Detector
4 Laser beam application unit
10 Sample
11 Sample ion
21 Substrate
21a One surface
21b Other surface
22, 122 Frame
23 Conductive layer
24 Adhesion layer
24a, 24b Adhesive face
30 Screw
122a Insertion hole
L Laser beam
S Through-hole
T Adhesive tape
Ta Adhesive face

The invention claimed is:

1. A surface-assisted laser desorption/ionization method comprising:
   a first process of preparing a sample support having a substrate in which a plurality of through-holes passing from one surface thereof to the other surface thereof are provided and a conductive layer that is formed of a conductive material and covers at least the one surface;
   a second process of placing a sample on a sample stage, arranging the sample support on the sample such that the other surface faces the sample, and adding a solution for reducing viscosity of the sample to the sample; and
   a third process of applying a laser beam to the one surface and ionizing the sample moved from the other surface side to the one surface side via the through-holes due to a capillary phenomenon.

2. The surface-assisted laser desorption/ionization method according to claim 1, wherein the solution includes acetonitrile.

3. The surface-assisted laser desorption/ionization method according to claim 1, wherein the substrate is formed by anodizing a valve metal or silicon.

4. The surface-assisted laser desorption/ionization method according to claim 1, wherein each of the through-holes has a width of 1 to 700 nm.

5. The surface-assisted laser desorption/ionization method according to claim 1, wherein the substrate has a thickness of 5 to 10 μm.

6. The surface-assisted laser desorption/ionization method according to claim 1, wherein the sample support further includes a frame mounted on an outer edge of the one surface of the substrate.

7. The surface-assisted laser desorption/ionization method according to claim 1, wherein in the second process, the sample support is fixed to the sample stage.

8. A mass spectrometry method comprising:
   each of the processes of the surface-assisted laser desorption/ionization method according to claim 1; and
   a fourth process of detecting the sample ionized in the third process,
   wherein the application of the laser beam in the third process and the detection of the ionized sample in the fourth process are performed at each application position while changing application positions of the laser beam.

9. A surface-assisted laser desorption/ionization method comprising:
   a first process of preparing a sample support having a substrate which is formed of a conductive material and in which a plurality of through-holes passing from one surface thereof to the other surface thereof are provided;

a second process of placing a sample on a sample stage, arranging the sample support on the sample such that the other surface is in contact with the sample, and adding a solution for reducing viscosity of the sample to the sample; and a third process of applying a laser beam to the one surface and ionizing the sample moved from the other surface side to the one surface side via the through-holes due to a capillary phenomenon.

10. The surface-assisted laser desorption/ionization method according to claim 9, wherein the solution includes acetonitrile.

* * * * *